(12) United States Patent
Kurunczi

(10) Patent No.: US 8,092,644 B2
(45) Date of Patent: Jan. 10, 2012

(54) METHOD AND APPARATUS FOR CLEANING AND SURFACE CONDITIONING OBJECTS USING PLASMA

(75) Inventor: Peter Frank Kurunczi, Beverly, MA (US)

(73) Assignee: IonField Systems, LLC, Moorestown, NJ (US)

( * ) Notice: Subject to any disclaimer, the term of this patent is extended or adjusted under 35 U.S.C. 154(b) by 1129 days.

(21) Appl. No.: 11/421,983

(22) Filed: Jun. 2, 2006

(65) Prior Publication Data
US 2006/0201534 A1 Sep. 14, 2006

Related U.S. Application Data

(60) Continuation-in-part of application No. 11/142,988, filed on Jun. 2, 2005, which is a continuation-in-part of application No. 11/143,083, filed on Jun. 2, 2005, now abandoned, which is a continuation-in-part of application No. 11/143,552, filed on Jun. 2, 2005, which is a continuation-in-part of application No. 11/043,787, filed on Jan. 26, 2005, now abandoned, which is a continuation-in-part of application No. 11/040,222, filed on Jan. 21, 2005, now abandoned, which is a continuation-in-part of application No. 11/036,628, filed on Jan. 20, 2005, now Pat. No. 7,017,594, which is a division of application No. 10/858,272, filed on Jun. 1, 2004, now Pat. No. 7,094,314.

(60) Provisional application No. 60/478,418, filed on Jun. 16, 2003.

(51) Int. Cl.
*B01L 1/00* (2006.01)
*C23F 3/00* (2006.01)

(52) U.S. Cl. .............. 156/345.43; 156/345.44; 422/553; 422/186.04
(58) Field of Classification Search ............... 134/1, 1.1; 219/121.43, 121.52; 156/345.43, 345.44; 204/164; 422/186.04, 551, 552, 553
See application file for complete search history.

(56) References Cited

U.S. PATENT DOCUMENTS
5,099,100 A 3/1992 Bersin et al.
(Continued)

FOREIGN PATENT DOCUMENTS
EP 0798397 A2 10/1997

OTHER PUBLICATIONS

*PCT International Preliminary Report on Patentability* mailed Jan. 5, 2006 for PCT Application No. PCT/US2004/17223.
(Continued)

*Primary Examiner* — Alexander Markoff
(74) *Attorney, Agent, or Firm* — Pepper Hamilton LLP

(57) ABSTRACT

An apparatus and method for cleaning objects using plasma are disclosed. The apparatus provides a plurality of elongated dielectric barrier members arranged adjacent each other, a plurality of electrodes each contained within, and extending substantially along the length of, the plurality of elongated dielectric barrier members, and at least one buss bar for electrically coupling the plurality of electrodes to a voltage source. The method provides providing a plurality of elongated dielectric barrier members arranged adjacent each other, providing a plurality of electrodes each contained within, and extending substantially along the length of the plurality of elongated dielectric barrier members, providing at least one buss bar connected to the plurality of electrodes, electrically coupling the plurality of electrodes to a voltage source through the at least one buss bar, introducing the objects proximate the plurality of elongated dielectric barrier members, generating a dielectric barrier discharge between the plurality of dielectric barrier members and the objects; and forming plasma to clean at least a portion of the objects.

18 Claims, 15 Drawing Sheets

U.S. PATENT DOCUMENTS

| | | | |
|---|---|---|---|
| 5,133,986 A | 7/1992 | Blum et al. | |
| 5,200,158 A | 4/1993 | Jacob | |
| 5,225,659 A | 7/1993 | Kusano et al. | |
| 5,236,672 A | 8/1993 | Nunez et al. | |
| 5,262,125 A | 11/1993 | Goodman | |
| 5,286,532 A | 2/1994 | Yoshikawa et al. | |
| 5,292,396 A | 3/1994 | Takashima et al. | |
| 5,414,324 A | 5/1995 | Roth et al. | |
| 5,451,428 A | 9/1995 | Rupp | |
| 5,573,732 A | 11/1996 | Waggener et al. | |
| 5,633,424 A | 5/1997 | Graves et al. | |
| 5,686,789 A | 11/1997 | Schoenbach et al. | |
| 5,700,327 A | 12/1997 | Babacz et al. | |
| 5,741,460 A | 4/1998 | Jacob et al. | |
| 5,876,663 A | 3/1999 | Laroussi | |
| 5,895,558 A | 4/1999 | Spence | |
| 5,897,831 A | 4/1999 | Jacob et al. | |
| 5,935,339 A | 8/1999 | Henderson et al. | |
| 5,939,829 A | 8/1999 | Schoenbach et al. | |
| 5,965,093 A | 10/1999 | Adams | |
| 6,059,935 A | 5/2000 | Spence | |
| 6,072,273 A | 6/2000 | Schoenbach et al. | |
| 6,105,589 A | 8/2000 | Vane | |
| 6,174,500 B1 | 1/2001 | Uno et al. | |
| 6,204,605 B1 | 3/2001 | Laroussi et al. | |
| 6,225,659 B1 | 5/2001 | Liu | |
| 6,283,130 B1 | 9/2001 | Tamura | |
| 6,342,187 B1 | 1/2002 | Jacob et al. | |
| 6,346,770 B1 | 2/2002 | Schoenbach et al. | |
| 6,403,029 B1 | 6/2002 | Schmidt | |
| 6,482,369 B2 | 11/2002 | Wang | |
| 6,518,692 B2 | 2/2003 | Schoenbach et al. | |
| 6,528,022 B1 | 3/2003 | Kinoshita | |
| 6,610,257 B2 | 8/2003 | Vane | |
| 6,624,413 B1 | 9/2003 | Klein | |
| 6,632,323 B2 | 10/2003 | Kim et al. | |
| 6,645,441 B1 | 11/2003 | Andrews et al. | |
| 6,652,816 B2 | 11/2003 | Hwang | |
| 6,664,737 B1 | 12/2003 | Berry et al. | |
| 6,666,928 B2 | 12/2003 | Worm | |
| 6,667,007 B1 | 12/2003 | Schmidt | |
| 6,692,704 B2 | 2/2004 | Nelson et al. | |
| 6,724,608 B2 | 4/2004 | Hensley et al. | |
| 6,784,424 B1 | 8/2004 | Willoughby et al. | |
| 6,818,193 B2 | 11/2004 | Christodoulatos et al. | |
| 6,977,722 B2* | 12/2005 | Wohlstadter et al. | 356/246 |
| 2001/0031234 A1 | 10/2001 | Christodoulatos et al. | |
| 2002/0020691 A1 | 2/2002 | Jewett et al. | |
| 2002/0036461 A1 | 3/2002 | Schoenbach et al. | |
| 2002/0076369 A1 | 6/2002 | Hwang | |
| 2002/0076370 A1 | 6/2002 | Wong et al. | |
| 2002/0124867 A1 | 9/2002 | Kim et al. | |
| 2002/0153241 A1* | 10/2002 | Niv et al. | 204/164 |
| 2002/0195950 A1 | 12/2002 | Mikhael et al. | |
| 2003/0015415 A1 | 1/2003 | Platt, Jr. et al. | |
| 2003/0052096 A1 | 3/2003 | Crowe et al. | |
| 2003/0072675 A1 | 4/2003 | Takeda et al. | |
| 2003/0098230 A1 | 5/2003 | Carlow et al. | |
| 2003/0106788 A1* | 6/2003 | Babko-Malyi | 204/164 |
| 2003/0116541 A1 | 6/2003 | Chiou et al. | |
| 2003/0129107 A1* | 7/2003 | Denes et al. | 422/186.21 |
| 2003/0132100 A1 | 7/2003 | Crowe et al. | |
| 2003/0155332 A1 | 8/2003 | Datta et al. | |
| 2004/0011764 A1 | 1/2004 | De Vries et al. | |
| 2004/0022945 A1 | 2/2004 | Goodwin et al. | |
| 2004/0037756 A1 | 2/2004 | Houston, Jr. et al. | |
| 2004/0045806 A1 | 3/2004 | Neff et al. | |
| 2004/0050685 A1 | 3/2004 | Yara et al. | |
| 2004/0052028 A1 | 3/2004 | O'Reilly et al. | |
| 2004/0112537 A1 | 6/2004 | Yamazaki et al. | |
| 2004/0134890 A1 | 7/2004 | Uhm et al. | |
| 2004/0148860 A1 | 8/2004 | Fletcher | |
| 2004/0185396 A1 | 9/2004 | Rosocha et al. | |
| 2004/0195088 A1 | 10/2004 | Rostaing et al. | |
| 2004/0231926 A1 | 11/2004 | Sakhrani et al. | |
| 2004/0238124 A1 | 12/2004 | Nakamura | |

OTHER PUBLICATIONS

*PCT International Search Report* mailed Jul. 8, 2005 for PCT Application No. PCT/US04/17223.

*PCT Written Opinion of the International Searching Authority* mailed Jul. 8, 2005 for PCT Application No. PCT/US04/17223.

"Well Positions for Microplates", *The Society for Biomolecular Screening, Publication ANSI/SBS*, Apr. 2004, www.sbsonline.com.

Braithwaite, N. St. J., "Introduction to gas discharges", *Plasma Sources Science and Technology*, 9, IOP Publishing Ltd. (2000), 517-527.

Conrads, H, et al., "Plasma generation and plasma sources", *Plasma Sources Science and Technology*, 9, IOP Publishing Ltd. (2000), 441-454.

Kogelschatz, U., "Dielectric-barrier Discharges: Their History, Discharge Physics, and Industrial Applications", *Plasma Chemistry and Plasma Processing*, 23 (1), Plenum Publishing Corporation (Mar. 1, 2003).

Kogelschatz, U., et al., "Dielectric-Barrier Discharges. Principle and Applications", *J. Phys IV France* (1997), C4-47 to C4-66.

Kogelschatz, U., "Filamentary, Patterned and Diffuse Barrier Discharges", *IEEE Transactions on Plasma Science*, 30 (4) (Aug. 2002).

Veldhuizen, E. M., et al., "Corona discharges: fundamentals and diagnostics", Invited Paper, *Proceedings of Frontiers in Low Temperature Plasma Diagnostics IV*, Rolduc, The Netherlands (Mar. 2001), 40-49.

*International Search Report* mailed Nov. 30, 2006 for PCT International Application No. PCT/US2006/021309.

Written Opinion mailed Nov. 30, 2006 for PCT International Application No. PCT/US2006/021309.

* cited by examiner

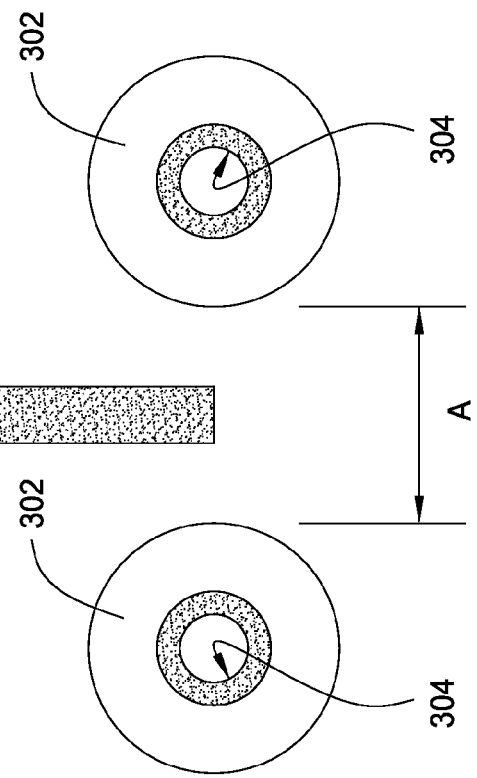
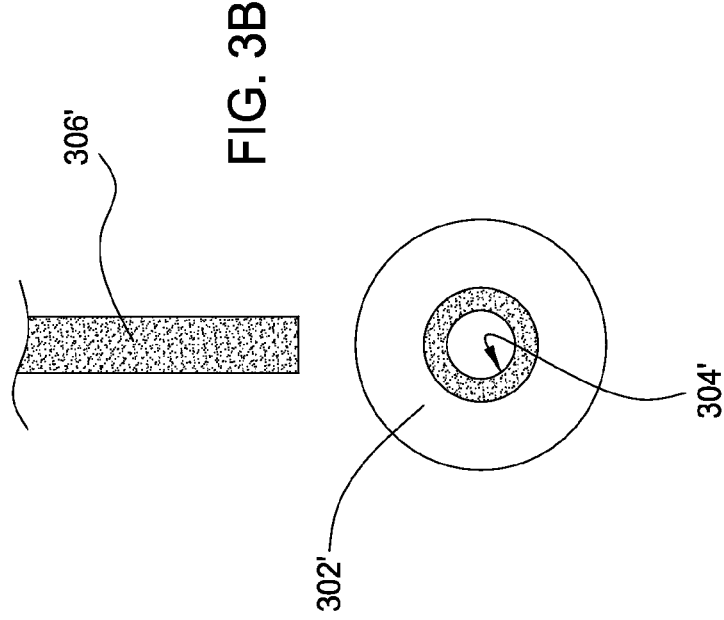

METHOD AND APPARATUS FOR CLEANING AND SURFACE CONDITIONING OBJECTS USING PLASMA

CROSS-REFERENCE TO RELATED APPLICATIONS

This application is a continuation-in-part of U.S. patent application Ser. No. 11/142,988, filed Jun. 2, 2005, which is a continuation-in-part of U.S. patent application Ser. No. 11/143,083, filed Jun. 2, 2005, which is a continuation-in-part of U.S. patent application Ser. No. 11/143,552, filed Jun. 2, 2005, which is a continuation-in-part of U.S. patent application Ser. No. 11/043,787, filed Jan. 26, 2005, which is a continuation-in-part of U.S. patent application Ser. No. 11/040,222, filed Jan. 21, 2005, which is a continuation-in-part of U.S. patent application Ser. No. 11/039,628, filed Jan. 20, 2005, now U.S. Pat. No. 7,017,594, which is a divisional of U.S. patent application Ser. No. 10/858,272, filed Jun. 1, 2004, which application claims the benefit of U.S. Provisional Patent Application Ser. No. 60/478,418, filed on Jun. 16, 2003, all prior applications of which are incorporated herein by reference in their entirety.

BACKGROUND OF THE INVENTION

1. Field of the Invention

Embodiments of the present invention generally relate to a method and apparatus for cleaning and surface conditioning fluid handling devices.

2. Description of the Related Art

In certain clinical, industrial and life science testing laboratories, extremely small quantities of fluids, for example, volumes between a drop (about 25 micro-liters) and a few nano-liters may need to be analyzed. Several known methods are employed to transfer these small amounts of liquid compounds from a source to a testing device. Generally, liquid is aspirated from a fluid holding device into a fluid handling device. The fluid handling device may include, but is not limited to, a probe, cannula, disposable pipette, pin tool or other similar component or plurality of such components (hereinafter collectively referred to as "probes"). The fluid handling device and its probes may move, manually, automatically or robotically, dispensing the aspirated liquid into another fluid holding device for testing purposes and the like.

Commonly, the probes, unless disposable, are reused from one test to the next. As a result, at least the tips of the probes must be cleaned between each test to avoid cross contamination. Conventionally, the probes undergo a wet "tip wash" process. That is, they are cleaned in between uses with a liquid solvent, such as Dimethyl Sulfoxide (DMSO), or at times simply water.

These methods and apparatus for cleaning and conditioning fluid handling devices have certain disadvantages. For example, the wet "tip wash" process takes a relatively long amount of time. This process can also be ineffective in sufficiently cleaning the probe tips between tests. Furthermore, disposing the used solvents from the wet process presents many issues and challenges, not the least of which is environmental.

Thus, there is a need for improved methods and apparatus for cleaning and surface conditioning fluid handling devices.

SUMMARY OF THE INVENTION

The present invention generally relates to an apparatus and method for cleaning at least a portion of a fluid handling device, which device includes a plurality of probes, using plasma.

In accordance with an embodiment of the present invention, there is provided an apparatus for cleaning objects using plasma, comprising a plurality of elongated dielectric barrier members arranged adjacent each other, a plurality of electrodes, each electrode contained within and extending substantially along the length of the plurality of elongated dielectric barrier members, and at least one buss bar for electrically coupling the plurality of electrodes to a voltage source.

In accordance with another embodiment of the present invention, there is provided an apparatus for cleaning objects using plasma, comprising a plurality of elongated dielectric barrier members arranged adjacent each other, a plurality of electrodes each contained within, and extending substantially along the length of, the plurality of elongated dielectric barrier members, and at least one buss bar for electrically coupling the plurality of electrodes to a voltage source, wherein the at least one buss bar comprises a conductive member and a flexible support member proximate the conductive member and proximate the plurality of dielectric barrier members, wherein the flexible support member substantially decouples movement of the plurality of dielectric barrier members and respective electrodes from the conductive member of the at least one buss bar.

In accordance with another embodiment, there is provided a method for cleaning objects using plasma, comprising providing a plurality of elongated dielectric barrier members arranged adjacent each other, providing a plurality of electrodes each contained within, and extending substantially along the length of, the plurality of elongated dielectric barrier members, providing at least one buss bar connected to the plurality of electrodes, electrically coupling the plurality of electrodes to a voltage source through the at least one buss bar, introducing the objects proximate the plurality of elongated dielectric barrier members, generating a dielectric barrier discharge between the plurality of dielectric barrier members and the objects, and forming plasma to clean at least a portion of the objects.

BRIEF DESCRIPTION OF THE DRAWINGS

So the manner in which the above recited features of the present invention can be understood in detail, a more particular description of embodiments of the present invention, briefly summarized above, may be had by reference to embodiments, some of which are illustrated in the appended drawings. It is to be noted; however, the appended drawings illustrate only typical embodiments of embodiments of the present invention and are therefore not to be considered limiting of its scope, for the present invention may admit to other equally effective embodiments.

FIG. 3A is a cross sectional schematic view of the device and a conductive probe of FIG. 1A showing the dimensions and spacing among the components;

FIG. 3B is a cross sectional schematic view of the device of FIG. 1A showing a conductive probe proximate the top of a dielectric barrier member;

Figure 1A:
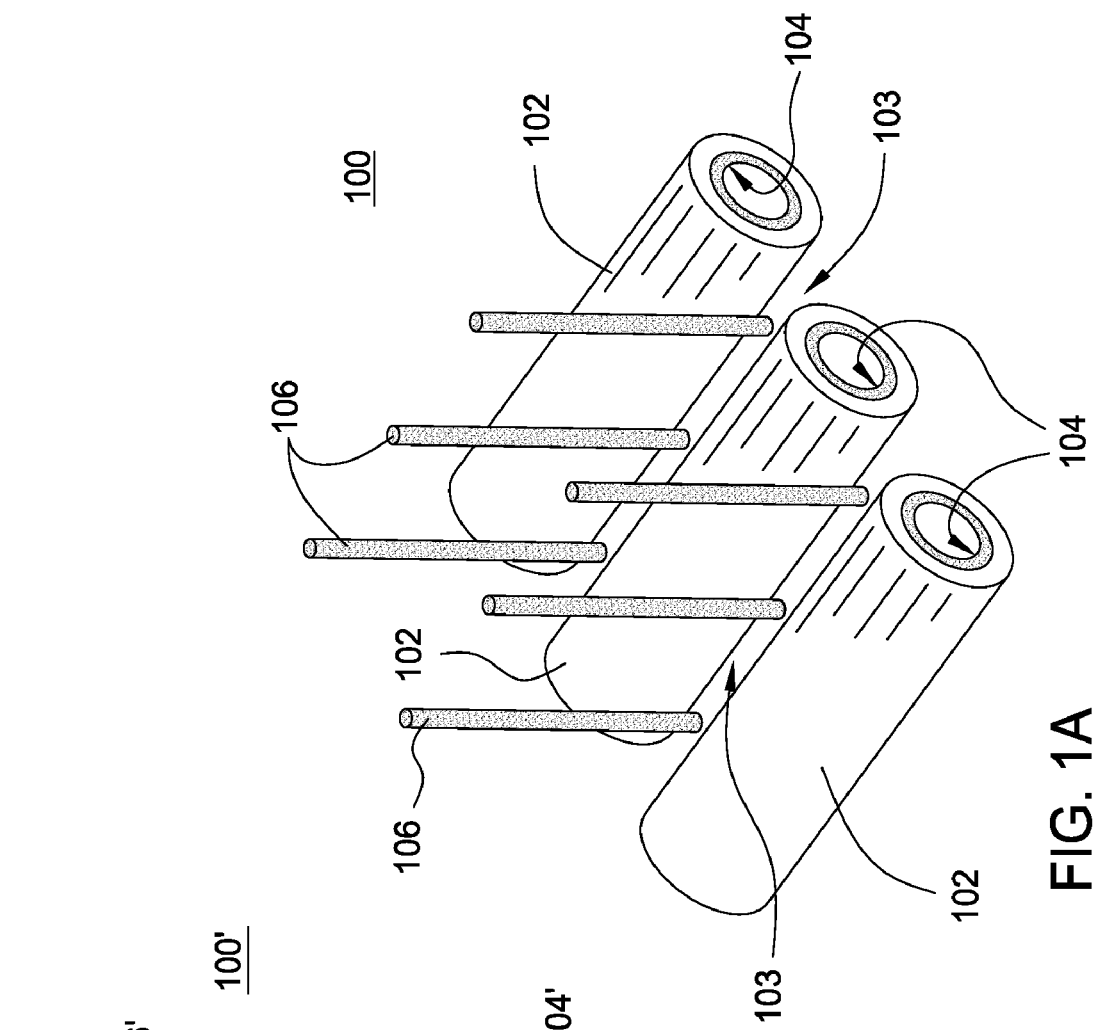
FIG. 1A is a top, partial perspective view of a plurality of conductive probes being introduced to a plurality of elongated dielectric barrier members with coupled inner electrodes in accordance with an embodiment of the present invention.

While embodiments of the present invention are described herein by way of example using several illustrative drawings, those skilled in the art will recognize the present invention is not limited to the embodiments or drawings described. It should be understood the drawings and the detailed description thereto are not intended to limit the present invention to the particular form disclosed, but to the contrary, the present invention is to cover all modification, equivalents and alternatives falling within the spirit and scope of embodiments of the present invention as defined by the appended claims.

The headings used herein are for organizational purposes only and are not meant to be used to limit the scope of the description or the claims. As used throughout this application, the word "can" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

The term "plasma" is used to describe a quasi-neutral gas of charged and neutral species characterized by a collective behavior governed by coulomb interactions. Plasma is typically obtained when sufficient energy, higher than the ionization energy of the neutral species, is added to the gas causing ionization and the production of ions and electrons. The energy can be in the form of an externally applied electromagnetic field, electrostatic field, or heat. The plasma becomes an electrically conducting medium in which there are roughly equal numbers of positively and negatively charged particles, produced when the atoms/molecules in a gas become ionized.

A plasma discharge is produced when an electric field of sufficient intensity is applied to a volume of gas. Free electrons are then subsequently accelerated to sufficient energies to produce electron-ion pairs through inelastic collisions. As the density of electrons increase, further inelastic electron atom/molecule collisions will result in the production of further charged carriers and a variety of other species. The species may include excited and metastable states of atoms and molecules, photons, free radicals, molecular fragments, and monomers.

The term "metastable" describes a type of atom/molecule excited to an upper electronic quantum level. Here, quantum mechanical selection rules forbid a spontaneous transition to a lower level. As a result, such species have long, excited lifetimes. For example, whereas excited states with quantum mechanically allowed transitions typically have lifetimes on the order of about $10^{-9}$ to $10^{-8}$ seconds before relaxing and emitting a photon, metastable states can exist for about $10^{-6}$ to $10^1$ seconds. The long metastable lifetimes allow for a higher probability of the excited species to transfer their energies directly through a collision with another compound and result in ionization and/or dissociative processes.

The plasma species are chemically active and/or can physically modify the surface of materials and may therefore serve to form new chemical compounds and/or modify existing compounds. For example, the plasma species can modify existing compounds through ionization, dissociation, oxidation, reduction, attachment, and recombination.

A non-thermal, or non-equilibrium, plasma is one in which the temperature of the plasma electrons is higher than the temperature of the ionic and neutral species. Within atmospheric pressure, non-thermal plasma, there is typically an abundance of the aforementioned energetic and reactive particles (i.e., species), such as ultraviolet photons, excited and/or metastable atoms and molecules, atomic and molecular ions, and free radicals. For example, within air plasma, there are excited, metastable, and ionic species of $N_2$, $N$, $O_2$, $O$, free radicals such as $OH$, $HO_2$, $NO$, $O$, and $O_3$, and ultraviolet photons ranging in wavelengths from 200 to 400 nanometers resulting from $N_2$, $NO$, and $OH$ emissions. In addition to the energetic (fast) plasma electrons, embodiments of the present invention harness and use these "other" particles to clean and surface condition portions of liquid handling devices, such as probes, and the like.

Referring to FIG. 1A, a partial view of a non-thermal atmospheric pressure plasma cleaning device 100 in accordance with an embodiment of the present invention is disclosed. The device 100 includes a plurality of elongated dielectric barrier members 102 arranged in a matrix or array and lying in a single plane. The members 102 are substantially regularly spaced apart from each other and form a gap 103 between adjacent members 102.

Each dielectric barrier member 102 includes an inner electrode 104 extending within, and substantially along the length of, respective elongated dielectric barrier members 102. A plurality of conductive probes 106 are shown extending into the open spaces or gaps 103 between the plurality of dielectric barrier members 102. In one embodiment, the probes 102 may be part of a fluid handling device. As such, the probes 102 are attached to and extend from a fluid handling device (not shown), which may be part of a microtiter plate test bed set up. In other embodiments, the probes 102 may be any form of conductive element that would benefit from plasma cleaning and surface conditioning.

The elongated dielectric barrier members 102 are made of any type of material capable of providing a surface for a dielectric barrier discharge of atmospheric pressure plasma (described below). Dielectric barrier material useful in this embodiment of the present invention includes, but is not limited to, ceramic, glass, plastic, polymer epoxy, or a composite of one or more such materials, such as fiberglass or a ceramic filled resin (available from Cotronics Corp., Wetherill Park, Australia).

In one embodiment, a ceramic dielectric barrier is alumina or aluminum nitride. In another embodiment, a ceramic dielectric barrier is a machinable glass ceramic (available from Corning Incorporated, Corning, N.Y.). In yet another embodiment of the present invention, a glass dielectric barrier is a borosilicate glass (also available from Corning Incorporated, Corning, N.Y.). In still another embodiment, a glass dielectric barrier is quartz (available from GE Quartz, Inc., Willoughby, Ohio). In an embodiment of the present invention, a plastic dielectric barrier is polymethyl methacrylate (PLEXIGLASS and LUCITE, available from Dupont, Inc., Wilmington, Del.). In yet another embodiment of the present invention, a plastic dielectric barrier is polycarbonate (also available from Dupont, Inc., Wilmington, Del.). In yet another embodiment, a plastic dielectric barrier is a fluoropolymer (available from Dupont, Inc., Wilmington, Del.). In another embodiment, a plastic dielectric barrier is a polyimide film (KAPTON, available from Dupont, Inc., Wilmington, Del.). Dielectric barrier materials useful in the present invention typically have dielectric constants ranging between 2 and 30. For example, in one embodiment that uses a polyimide film plastic such as KAPTON, at 50% relative humidity, with a dielectric strength of 7700 Volts/mil, the film would have a dielectric constant of about 3.5.

The inner electrode 104 may comprise any conductive material, including metals, alloys and conductive compounds. In one embodiment, a metal may be used. Metals useful in this embodiment of the present invention include, but are not limited to, copper, silver, aluminum, and combinations thereof. In another embodiment of the present invention, an alloy of metals may be used as the inner electrode 104. Alloys useful in this embodiment of the present invention include, but are not limited to, stainless steel, brass, and bronze. In another embodiment of the present invention, a conductive compound may be used. Conductive compounds useful in the present invention include, but are not limited to, indium-tin-oxide.

The inner electrodes 104 of embodiments of the present invention may be formed using any method known in the art. In one embodiment of the present invention, the inner electrodes 104 may be formed using a foil. In another embodiment of the present invention, the inner electrodes 104 may be formed using a wire. In yet another embodiment of the present invention, the inner electrodes 104 may be formed using a solid block of conductive material. In another embodiment of the present invention, the inner electrodes 104 may be deposited as an integral layer directly onto the inner core of the dielectric barrier members 102. In one such embodiment, an inner electrode 104 may be formed using a conductive paint, which is applied to the inner core of the elongated dielectric barrier members 102.

In one use of the present invention, the conductive probes 106 are part of the fluid handling device and are introduced in the gap 103, i.e., proximate the elongated dielectric barrier members 102 of the plasma cleaning device 100. Use of the term "probe" is meant to include, but not be limited to, probes, cannulas, pin tools, pipettes and spray heads or any portion of a fluid handling device that is capable of carrying fluid. These portions are generally hollow to carry the fluid but may be solid and include a surface area capable of retaining fluid. All of these different types of fluid handling portions of a fluid handling device are collectively referred to in this application as "probes." In an embodiment, the probe is conductive and is made of conductive material similar to that material described above in connection with the inner electrode 104.

Figure 1B:
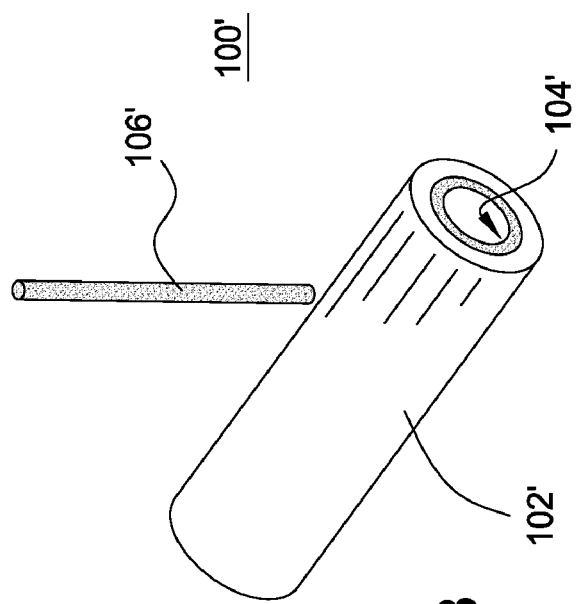
FIG. 1B is a top, partial perspective view of one conductive probe being introduced to one dielectric barrier member with a coupled inner electrode in accordance with an embodiment of the present invention.

FIG. 1B depicts a non-thermal atmospheric pressure plasma cleaning device 100' in accordance with another embodiment of the present invention. In this embodiment, a dielectric barrier member 102' and one inner electrode 104' are shown. In addition, one conductive probe 106' is shown being introduced proximate the dielectric 102'. Each conductive probe 106 may be introduced proximate one (FIG. 1B) or many (FIG. 1A) elongated dielectric barrier members 102. When each conductive probe 106 is proximate one elongated dielectric barrier member 102, the conductive probe 106 may be introduced proximate the top of the elongated dielectric barrier member 102. When each conductive probe 106 is introduced proximate two elongated dielectric barrier members 102, the conductive probe 106 may be introduced either proximate or between the two elongated dielectric barrier members 102 (as shown in FIG. 1A).

Figure 2:
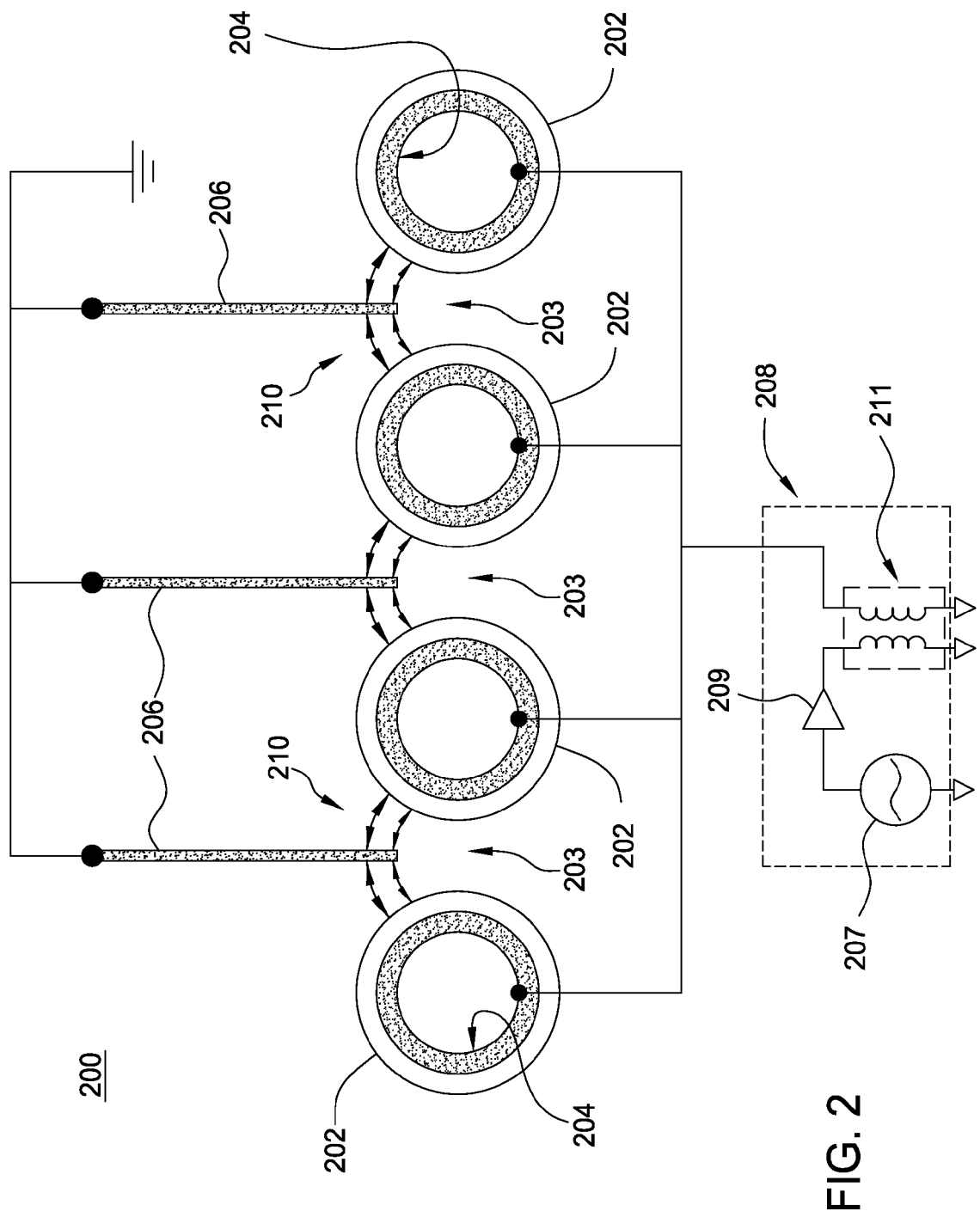
FIG. 2 is a front, expanded view of the device and the conductive probes of FIG. 1A showing the components electrically coupled.

Referring to FIG. 2, a cross sectional portion of an atmospheric pressure plasma device is designated as 200. The portion 200 shown includes a plurality of inner electrodes 204 of each elongated dielectric barrier member 202 electrically connected to an AC voltage source 208. The conductive probes 206 are electrically grounded with respect to the AC voltage source 208. The AC voltage source 208 in this embodiment includes an AC source 207, a power amplifier 209 and a transformer 211 to supply voltage to the inner electrodes 204.

In certain embodiments of the atmospheric pressure plasma device 200, a dielectric barrier discharge (DBD) (also known as a "silent discharge") technique is used to create microdischarges of atmospheric pressure plasma. In a DBD technique, a sinusoidal voltage from an AC source 207 is applied to at least one inner electrode 204, within an insulating dielectric barrier member 202. Dielectric barrier discharge techniques have been described in "Dielectric-barrier Discharges: Their History, Discharge Physics, and Industrial Applications", Plasma Chemistry and Plasma Processing, Vol. 23, No. 1, March 2003, and "Filamentary, Patterned, and Diffuse Barrier Discharges", IEEE Transactions on Plasma Science, Vol. 30, No. 4, August 2002, both authored by U. Kogelschatz, the entire disclosures of which are incorporated by reference herein.

A substantially uniform atmospheric pressure plasma in air is obtained by placing a dielectric barrier in between the electrode 204 and the conductive probe 206 to control the discharge, i.e., choke the production of atmospheric pressure plasma. That is, before the discharge can become an arc, the dielectric barrier 202 chokes the production of the discharge. Because this embodiment is operated using an AC voltage source, the discharge oscillates in a sinusoidal cycle. The microdischarges generally occur near the peak of each sinusoid. One advantage to this embodiment is that controlled, non-equilibrium plasmas can be generated at atmospheric pressure using a relatively simple and efficient technique.

In operation, the AC voltage source 208 applies a sinusoidal voltage to the inner electrodes 204. Then, the plurality of conductive probes 206 are introduced into the gap 203 between adjacent elongated dielectric barriers 202. A dielectric barrier discharge (DBD) is produced. This DBD forms atmospheric pressure plasma, represented by arrows 210. In an embodiment of the present invention, atmospheric pressure plasma is obtained when, during one phase of the applied AC voltage, charges accumulate between the dielectric surface and the opposing electrode until the electric field is sufficiently high enough to initiate an electrical discharge through the gas gap (also known as "gas breakdown").

During an electrical discharge, an electric field from the redistributed charge densities may oppose the applied electric field and the discharge is terminated. In one embodiment, the applied voltage-discharge termination process may be repeated at a higher voltage portion of the same phase of the applied AC voltage or during the next phase of the applied AC voltage. A point discharge generally develops within a high electric field region near the tip of the conductive probe 206.

To create the necessary DBD for an embodiment of the present invention, the AC voltage source 208 includes an AC power amplifier 209 and a high voltage transformer 211. The frequency ranges from about 10,000 Hertz to 20,000 Hertz, sinusoidal. The power amplifier has an output voltage of from about 0 Volts (rms) to about 22.5 Volts (rms) with an output power of 500 watts. The high voltage transformer ranges from about 0 V (rms) to about 7,000 Volts (rms) (which is about 10,000 volts (peak)). Depending on the geometry and gas used for the plasma device, the applied voltages can range from about 500 to about 10,000 Volts (peak), with frequencies ranging from line frequencies of about 50 Hertz up to about 20 Megahertz.

In an embodiment of the present invention, the frequency of a power source may range from about 50 Hertz up to about 20 Megahertz. In another embodiment of the present invention, the voltage and frequency may range from about 5,000 to about 15,000 Volts (peak) and about 50 Hertz to about 50,000 Hertz, respectively.

The gas used in the plasma device 200 of the present invention can be ambient air, pure oxygen, any one of the rare gases, or a combination of each such as a mixture of air or oxygen with argon and/or helium. Also, the gas may include an additive, such as hydrogen peroxide, or organic compounds such as methanol, ethanol, ethylene or isopropynol to enhance specific atmospheric pressure plasma cleaning properties.

FIG. 3A depicts an example of the geometry and relationship among components in accordance with an embodiment of the present invention. The elongated dielectric barrier member 302 (shown in cross section) may comprise, for example, an elongated hollow tube with a hollow inner electrode 304 extended substantially the length of the elongated dielectric barrier member 302. Alternatively, the elongated dielectric barrier member 302 may be solid with a solid inner electrode 304. The elongated dielectric barrier 302 may comprise different shapes as well. For example, and not in any way limiting the scope of the present invention, the shape of the elongated dielectric barrier may be, by way of example only, tubular, circular, square, rectangular, oval, polygonal, triangular, trapezoidal, rhombus and irregular. If tubular, each dielectric barrier tube is about 2 mm in diameter and 75 to 120 mm long.

In this embodiment, the elongated dielectric barrier members 302 are placed adjacent one another, defining a plane. They are spaced at regular intervals and form a gap 303, designated as spacing A. Alternatively, the members 302 can be staggered in a non-planar arrangement with respect to one another. The spacing A is sized to allow at least a portion of each of the plurality of probes to be introduced proximate or between the elongated dielectric barrier members.

The gap 303 or spacing A can approach zero, provided there is a sufficient gap to allow air or other gas mixture to flow through the elongated dielectric barrier members 302. Spacing A or gap 303 can range from about 0 mm to about 10 mm. The spacing A or gap 303 may also range from about 2 mm to about 9.5 mm. In one embodiment, the spacing A is equal to about 9 mm. In another embodiment, the spacing A is equal to about 4.5 mm. In yet another embodiment, the spacing A is equal to about 2.25 mm.

In an embodiment, where both the probes 306 and the plurality of elongated dielectric barrier members 302 are substantially tubular (each having substantially the same respective diameter) and the plurality of probes 306 are substantially tubular (each having substantially the same respective diameter), the probe 306 diameter is relatively smaller than the diameter of the plurality of elongated dielectric barrier members. Thus, even if the spacing A (or gap 303) between the elongated dielectric barrier members 302 approaches 0 mm, the probes 306 are still capable of being introduced proximate, if not between, a pair of elongated dielectric members 302, sufficient to be exposed to a DBD.

Alternatively, as shown in FIG. 3B, the probes 306' can be introduced generally proximate the top of each elongated dielectric barrier member 302'. FIG. 3B depicts only one probe 306' and one dielectric 302' but it is to be understood the present invention contemplates a plurality of probes 306' being introduced proximate the top of a plurality of respective dielectric barrier members 302'.

Figure 4:
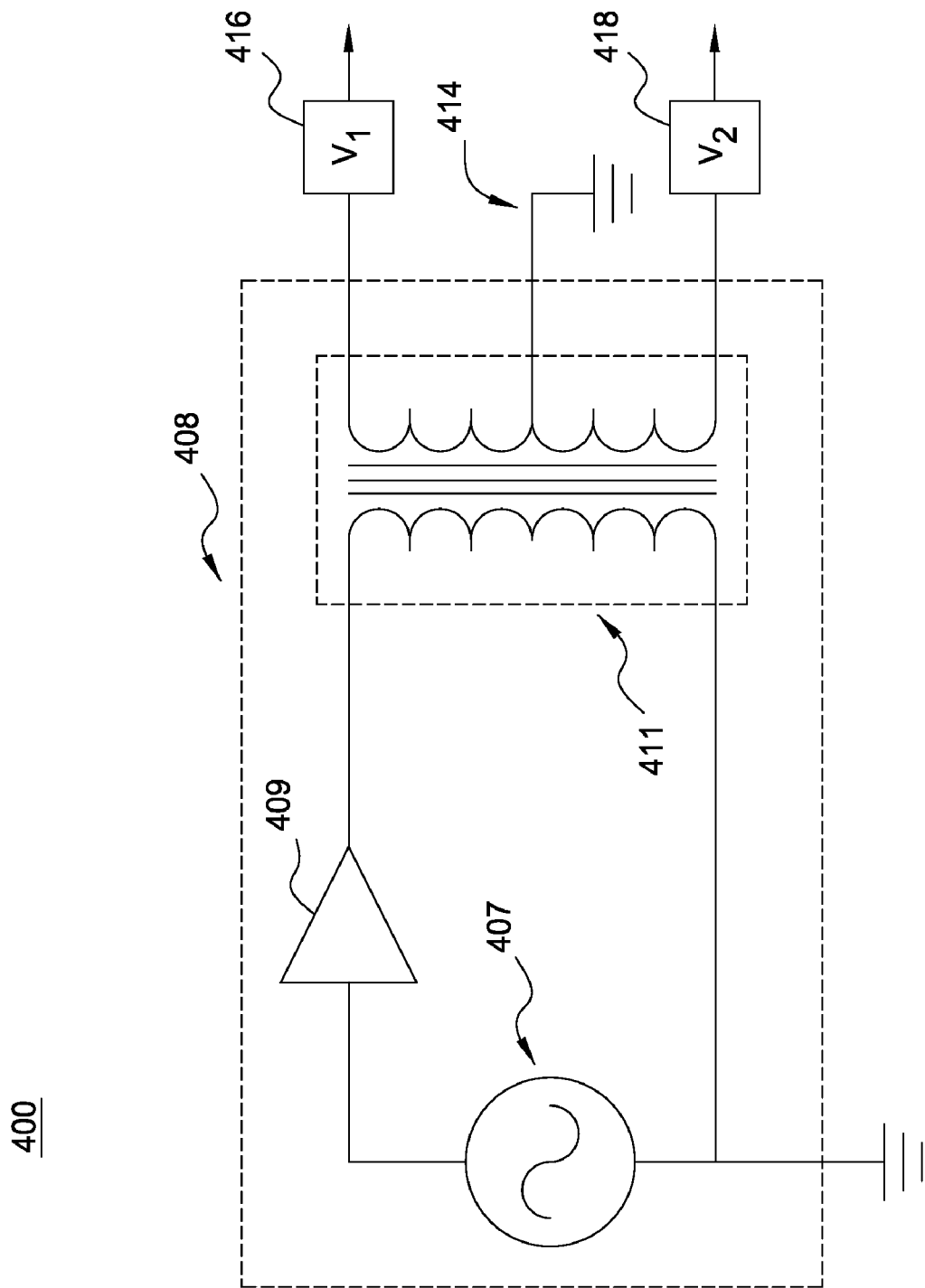
FIG. 4 is a schematic view of an alternative power supply in accordance with another embodiment of the present invention.

FIG. 4 is a schematic view of an alternative power supply in accordance with another embodiment of the present invention. Here, the power supply comprises a voltage source 408. The voltage source 408 comprises an AC source 407, a power amplifier 409 and a center tapped transformer 411 to provide two voltage potentials from a center tapped ground 414. The first voltage ($V_1$) 416 is coupled to a first set of elongated dielectric barrier members and the second voltage ($V_2$) 418 is coupled to a second set of elongated dielectric barrier members, as shown in FIGS. 5 and 6 and described herein.

Figure 5:
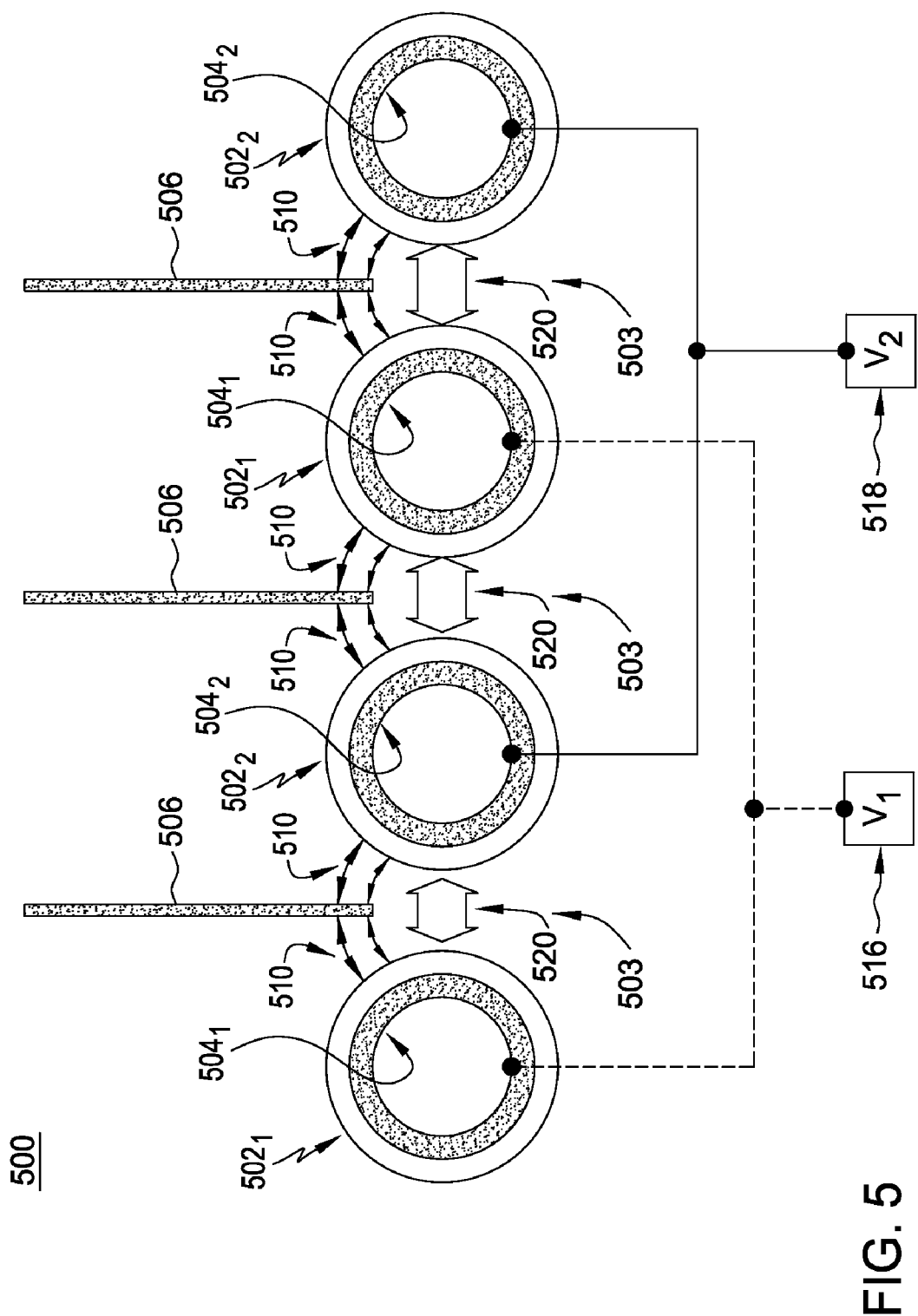
FIG. 5 is a front, expanded view of the device and the conductive probes of FIG. 1A, the device being electrically coupled to the power supply of FIG. 4.
Figure 6:
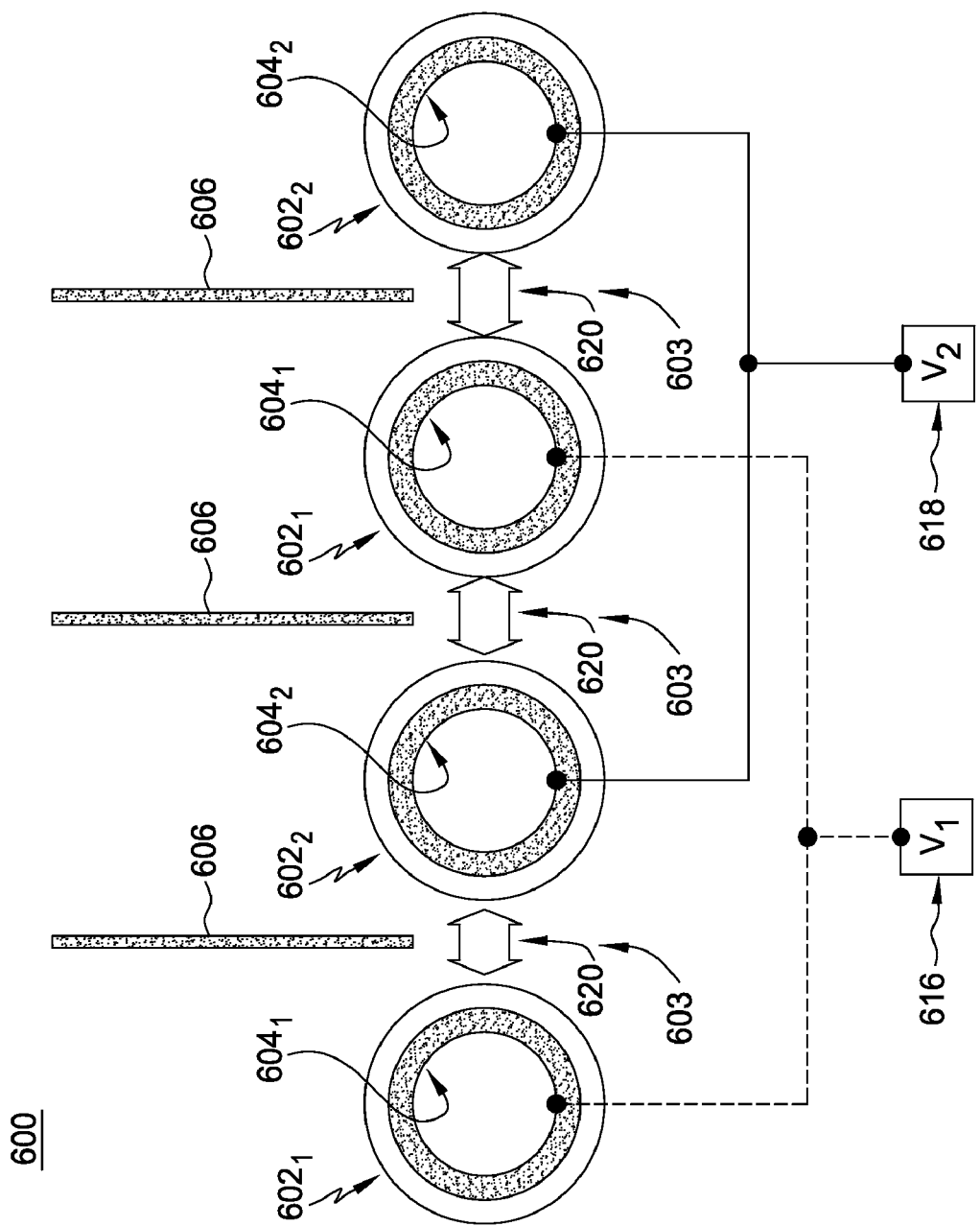
FIG. 6 is a front, expanded view of a device of FIG. 5, with non-conductive, or electrically isolated probes, the device being electrically coupled to the power supply of FIG. 4.

FIG. 5 is a cross sectional portion of an atmospheric pressure plasma device 500 coupled to the voltage source 408 including the center tapped transformer 411, as described in FIG. 4, in accordance with another embodiment of the present invention. The portion 500 comprises a first plurality of inner electrodes $504_1$ of each elongated dielectric barrier member $502_1$ electrically connected to the voltage source 408 via a first voltage (V1) 516. The portion 500 further comprises a second plurality of inner electrodes $504_2$ of each elongated dielectric barrier member $502_2$ electrically connected to the voltage source 408 via the second voltage ($V_2$) 518. The conductive probes 506 are electrically grounded with respect to the voltage source 408. The voltage source 408 supplies the two voltages to the inner electrodes 504. In this alternative embodiment, for example, $V_1=-V_2$.

As shown in FIG. 5, a dielectric barrier discharge (DBD) technique is again used to create microdischarges of atmospheric pressure plasma. In the DBD technique, two equal and opposite sinusoidal voltages from the AC source 407 are applied to the first and second sets, respectively, of at least one pair of inner electrodes 504, within corresponding insulating dielectric barrier members 502.

Substantially uniform atmospheric pressure plasma in air is obtained by placing dielectric barriers $502_1$ and $502_2$ in between the electrodes $504_1$ and $504_2$, respectively, and the conductive probes 506 to control the discharge, i.e., choke the production of atmospheric pressure plasma. That is, before the discharge can become an arc, the dielectric barriers 502 choke the production of the discharge. Because this embodiment is operated using an AC voltage source having two voltage potentials, the discharge oscillates in two substantially corresponding sinusoidal cycles. The microdischarges generally occur near the peak of each sinusoid.

In operation, the voltage source 408 applies two sinusoidal voltages $V_1$ and $V_2$ to the inner electrodes $504_1$ and $504_2$, respectively. Then, the plurality of conductive probes 506 are introduced into the gap 503 between adjacent elongated dielectric barriers $502_1$ and $502_2$. A DBD is produced. This DBD forms atmospheric pressure plasma, represented by arrows 510. In addition to this DBD, an additional discharge 520 is produced. This is due to the voltage difference between adjacent inner electrodes $504_1$ and $504_2$. This additional discharge is represented by the larger arrows.

To create the necessary DBDs 510 and 520 for an embodiment of the present invention, the voltage source 408 includes the AC power amplifier 409 and the high voltage center tapped transformer 411. Similar to the source 208 of FIG. 2, the frequency ranges from about 10,000 Hertz to 20,000 Hertz, sinusoidal. The power amplifier 409 has an output voltage of from about 0 Volts (rms) to about 22.5 Volts (rms) with an output power of about 500 watts. The high voltage center tapped transformer 411 ranges from about −4000 Volts (rms) to about 4,000 Volts (rms). Depending on the geometry and gas used for the plasma device, the applied voltages can range from about 500 to about 10,000 Volts (peak), with frequencies ranging from line frequencies of about 50 Hertz up to about 20 Megahertz. Here, the total voltage between the dielectric barriers is about 10,000 Volts, while the probe will only see about 5,000 Volts.

In an embodiment of the present invention, the frequency of a power source may range from about 50 Hertz up to about 20 Megahertz. In another embodiment of the present invention, the voltage and frequency may range from about 5,000 to about 15,000 Volts (peak) and about 50 Hertz to about 50,000 Hertz, respectively.

The gas used in the plasma device 500 of the present invention can be ambient air, pure oxygen, any one of the rare gases, or a combination of each such as a mixture of air or oxygen with argon and/or helium. Also, the gas may include an additive, such as hydrogen peroxide, or organic compounds such as methanol, ethanol, ethylene or isopropynol to enhance specific atmospheric pressure plasma cleaning properties.

FIG. 6 is a cross sectional portion of an atmospheric pressure plasma device 600 coupled to the voltage supply 408 including the center tapped transformer 411, as described in FIG. 4, in accordance with yet another embodiment of the present invention. The portion 600 comprises a first plurality of inner electrodes $604_1$ of each elongated dielectric barrier member $602_1$ electrically connected to the voltage source 408 via a first voltage ($V_1$) 616. The portion 600 further comprises a second plurality of inner electrodes $604_2$ of each elongated dielectric barrier member $602_2$ electrically connected to the voltage source 408 via the second voltage ($V_2$) 618. Here, the probes 606 are non-conductive, or conductive but electrically isolated, and are therefore not electrically grounded with respect to the voltage source 408. The voltage source 408 supplies the two voltages to the inner electrodes 604. In this embodiment, for example, $V_1 = -V_2$.

As shown in FIG. 6, a dielectric DBD technique is again used to create microdischarges of atmospheric pressure plasma. In the DBD technique, two equal and opposite sinusoidal voltages from the AC source 407 are applied to the first and second sets, respectively, of at least one pair of inner electrodes 604, within corresponding insulating dielectric barrier members 602. Here, no DBD is formed between the dielectrics 602 and the probes 606 because the probes are non-conductive or electrically isolated. Instead, the DBD is only formed between paired dielectrics $602_1$ and $602_2$ because of the voltage difference between respective pairs of inner electrodes $604_1$ and $604_2$.

In operation, the voltage source 408 applies two sinusoidal voltages $V_1$ and $V_2$ to the inner electrodes $604_1$ and $604_2$, respectively. A DBD 620 is produced. This is due to the voltage difference between adjacent inner electrodes $604_1$ and $604_2$. This additional discharge is represented by the larger arrows. To create the necessary DBDs 620 for this embodiment of the present invention, the same requirements of the voltage source 408 as discussed above with respect to FIGS. 4 and 5 apply here. The gas used in the plasma device 600 of this embodiment of the present invention is similar to that discussed above with respect to FIG. 5.

Figure 7:
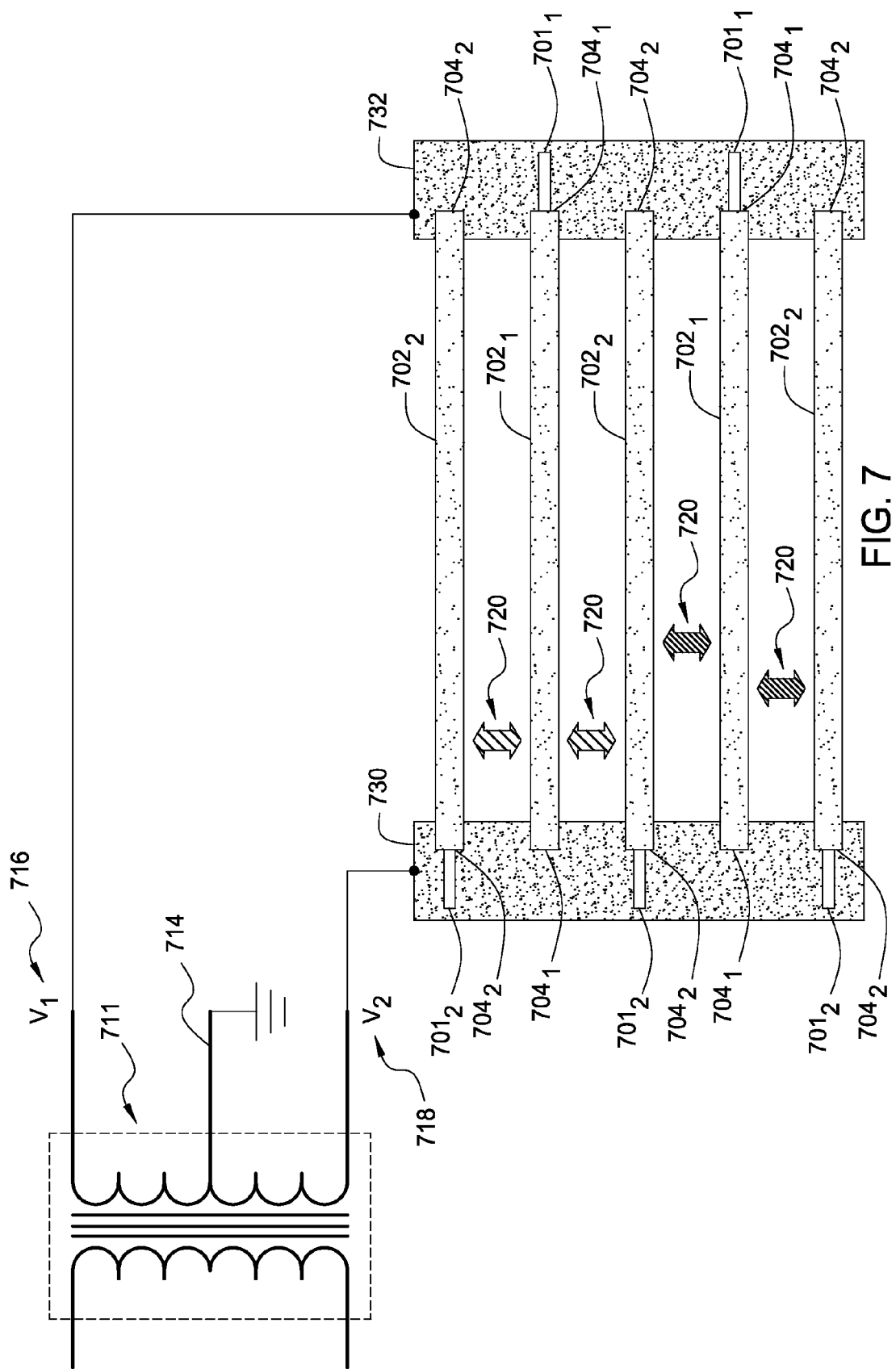
FIG. 7 is a partial, top plan view showing the staggered connection of electrical contacts to buss bars (contact planes) for use with the power supply shown in FIG. 4.

FIG. 7 is a partial, top plan view showing the staggered connection of electrical contacts to buss bars (contact planes) for use with a voltage source 408 similar to that shown in FIG. 4. The elongated dielectric barrier members $702_1$, $702_2$ may comprise either tubes or plates (or any other variation of shapes) as described hereinabove and in the commonly assigned patent applications discussed previously and incorporated herein by reference in their entirety.

As shown, the inner electrodes $704_1$ of the elongated dielectric members $702_1$ are electrically coupled to buss bar 732 via contacts $701_1$. The inner electrodes $704_2$ of the elongated dielectric members $702_2$ are electrically coupled to buss bar 730 via contacts $701_2$. As described before, in this configuration, plasma is formed between adjacent members $702_1$ and $702_2$ as designated by the large arrows 720.

Figure 8:
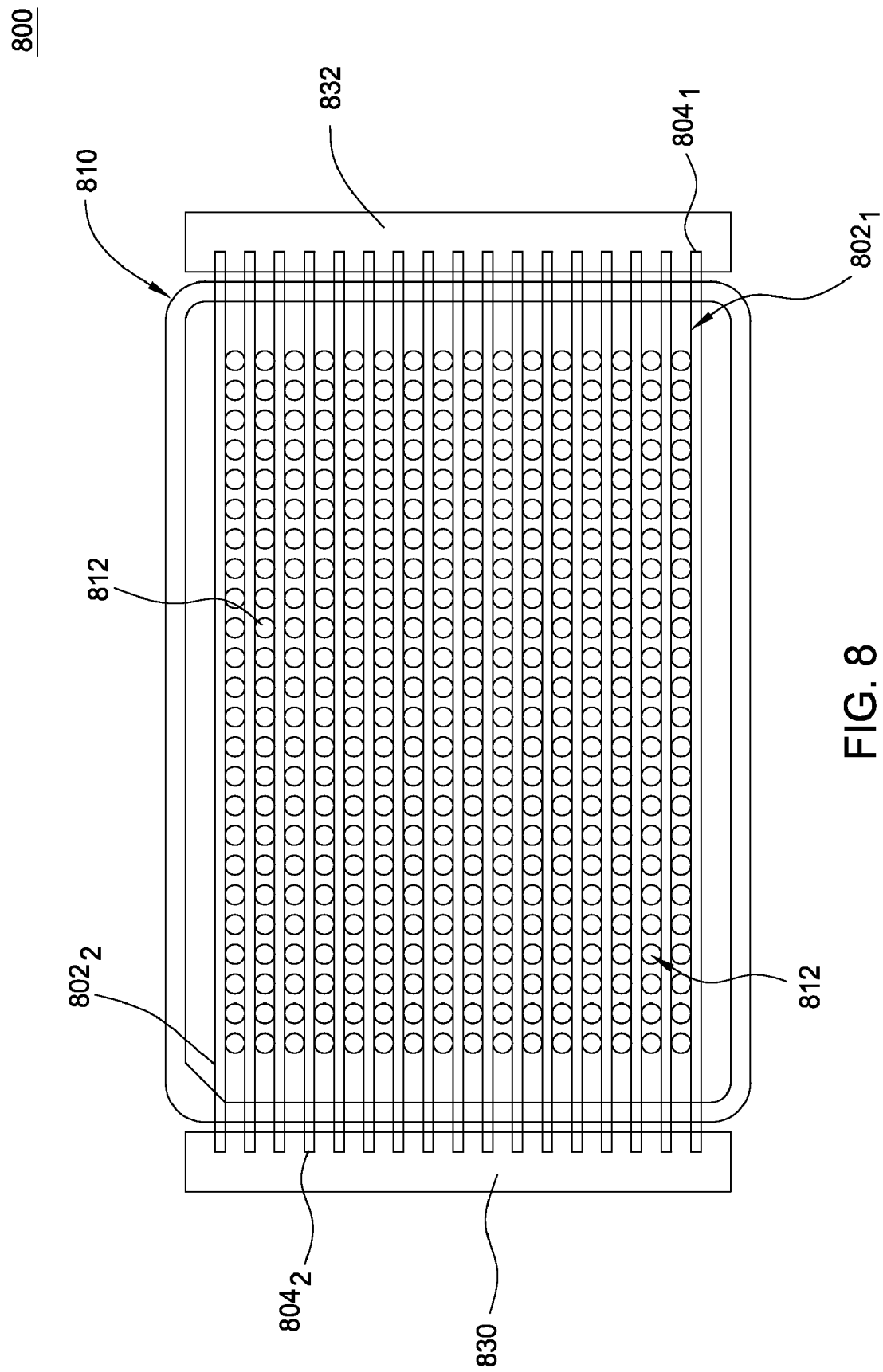
FIG. 8 is a is a top plan view of a matrix or array of elongated dielectric barrier members shown in the previous figures arranged in a microtiter plate format.

FIG. 8 is a top plan view of the above described plasma device of FIGS. 5 and 6 configured and arranged in a standard microtiter plate format 800. For example, the microtiter plate format may be sized to accommodate 96 openings for receiving a plurality of fluid handling probes. Alternatively, the microtiter plate is sized to accommodate 384 openings for receiving a plurality of probes. As an alternative, the wells and the pitch between rows of wells of the microtiter plate are sized to accommodate 1536 openings for receiving a plurality of probes.

Microtiter plates or microplates, similar to the one depicted in FIG. 8, are small, usually plastic, reaction vessels. The microplate 800 has a tray or cassette 810 covered with wells or dimples 812 arranged in orderly rows. These wells 812 are used to conduct separate chemical reactions during a fluid testing step. The large number of wells, which typically number 96, 384 (as shown in FIG. 8) or 1536, depending upon the well size and pitch between rows of wells of the microplate allow for many different reactions to take place at the same time. Microplates are ideal for high-throughput screening and research. They allow miniaturization of assays and are suitable for many applications, including drug testing, genetic study, and combinatorial chemistry.

The microplate 800 has been equipped with an embodiment of the present invention similar to the configuration discussed with reference to FIGS. 5 and 6. Situated in rows on the top surface of the microplate 800 and between the wells 812 are a plurality of elongated dielectric barrier members 802 similar to those described hereinabove.

The inner electrodes $804_1$ of the elongated dielectric barrier members $802_1$ are electrically coupled to $V_1$ of the voltage source through contact plane 832 of the cassette 810. The inner electrodes $804_2$ of the elongated dielectric barrier members $802_2$ are electrically coupled to $V_2$ of the AC voltage source through contact planes 830 of the cassette 810.

The elongated dielectric barrier members 802 are respectively spaced apart in this embodiment a pitch of about 4.5 mm. In alternative embodiments, where the well count is 96, the members 802 are spaced apart a pitch of about 9 mm. In yet another embodiment, where the wells 812 numbered 1536, the pitch is 2.25 mm. During a cleaning step, the wells 812 of the microplate 800 do not necessarily function as liquid holding devices. Rather, the wells 812 are used to allow receiving space for the probes when the probes are fully introduced between the elongated dielectric barrier members 802.

In operation, the microplate 800 is placed in, for example, a deck mounted wash station. In, for example, an automated microplate liquid handling instrumentation, the system performs an assay test. Then, at least the probe tips of the fluid handling device require cleaning. As such, the fluid handling device enters the wash station. A set of automated commands initiate and control the probes to be introduced to the microplate 800 proximate the stacked elongated dielectric barrier members 802. At or about the same time, the AC voltage power source is initiated. Alternatively, the power source remains on during an extended period.

During the power-on phase, as the probes are introduced to the elongated dielectric members 802 of the microplate 800, DBDs of plasma are formed between the members 802 and the probes (see, e.g., FIG. 5) or just between the members (see, e.g., FIG. 6).

In an embodiment of the present invention where the probes are hollow, the reactive and energetic components or species of the plasma are repeatedly aspirated into the probes, using the fluid handling devices' aspirating and dispensing capabilities. The aspiration volume, rate and frequency are determined by the desired amount of cleaning/sterilization required.

Any volatized contaminants and other products from the plasma may be vented through the bottom of the microplate 800 by coupling the bottom of the tray 810 to a region of negative pressure such as a modest vacuum. This vacuum may be in communication with the wells 812 and is capable of drawing down plasma and reactive byproducts through to the bottom of the device and into an exhaust manifold (not shown) of the cleaning station test set up.

In an embodiment, ions, excited and metastables species (corresponding emitted photons), and free radicals are found in the atmospheric pressure plasma and remain long enough to remove substantially all of the impurities and contaminates left from the previous test performed by the fluid handling device's probes. These particle species remain longer (see FIG. 9) than the initial plasma formed from a DBD or microdischarge and are therefore effective in cleaning the probes in preparation for the next test as the initially formed plasma itself.

Figure 9:
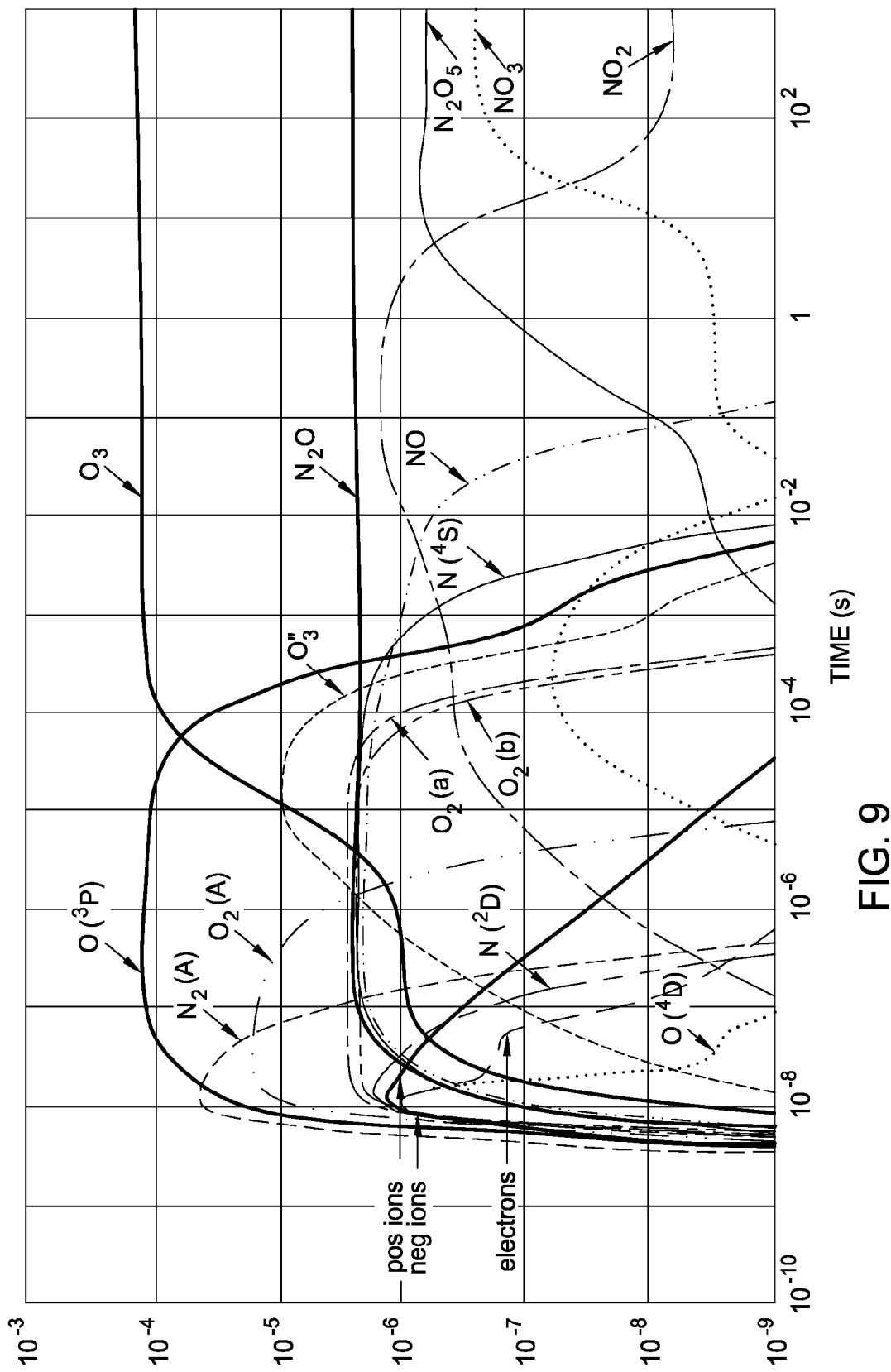
FIG. 9 represents a graph of the relative concentrations of different chemical and particle species of plasma in time after the initiation of a single microdischarge that forms atmospheric pressure plasma in air.

In particular, FIG. 9 represents a graph of the relative concentrations of different particle species in time after the initiation of a single microdischarge forming atmospheric pressure plasma in air. Metastables are represented by $N_2(A)$ and $N_2(B)$. Free radicals are represented by $O_3$, $O(^3P)$, $N(^4S)$ and NO. Free radicals and metastables are represented by $O(^1D)$ and $N(^2D)$. In non-equilibrium microdischarges, the fast electrons created by the discharge mechanism mainly initiate the chemical reactions in the atmospheric pressure plasma. The fast electrons can inelastically collide with gas molecules and ionize, dissociate, and/or excite them to higher energy levels, thereby losing part of their energy, which is replenished by the electric field. The resulting ionic, free radical, and excited species can then, due to their high internal energies or reactivities, either dissociate or initiate other reactions.

In plasma chemistry, the transfer of energy, via electrons, to the species that take part in the reactions must be efficient. This can be accomplished by a very short discharge pulse. This is what occurs in a microdischarge. FIG. 9 shows the evolution of the different particle species initiated by a single microdischarge in "air" (80% $N_2$, plus 20% $O_2$). The short current pulse of roughly 10 ns duration deposits energy in various excited levels of $N_2$ and $O_2$, some of which lead to dissociation and finally to the formation of ozone and different nitrogen oxides. After about 50 ns, most charge carriers have disappeared and the chemical reactions proceed without major interference from charge carriers and additional gas heating.

Figure 10:
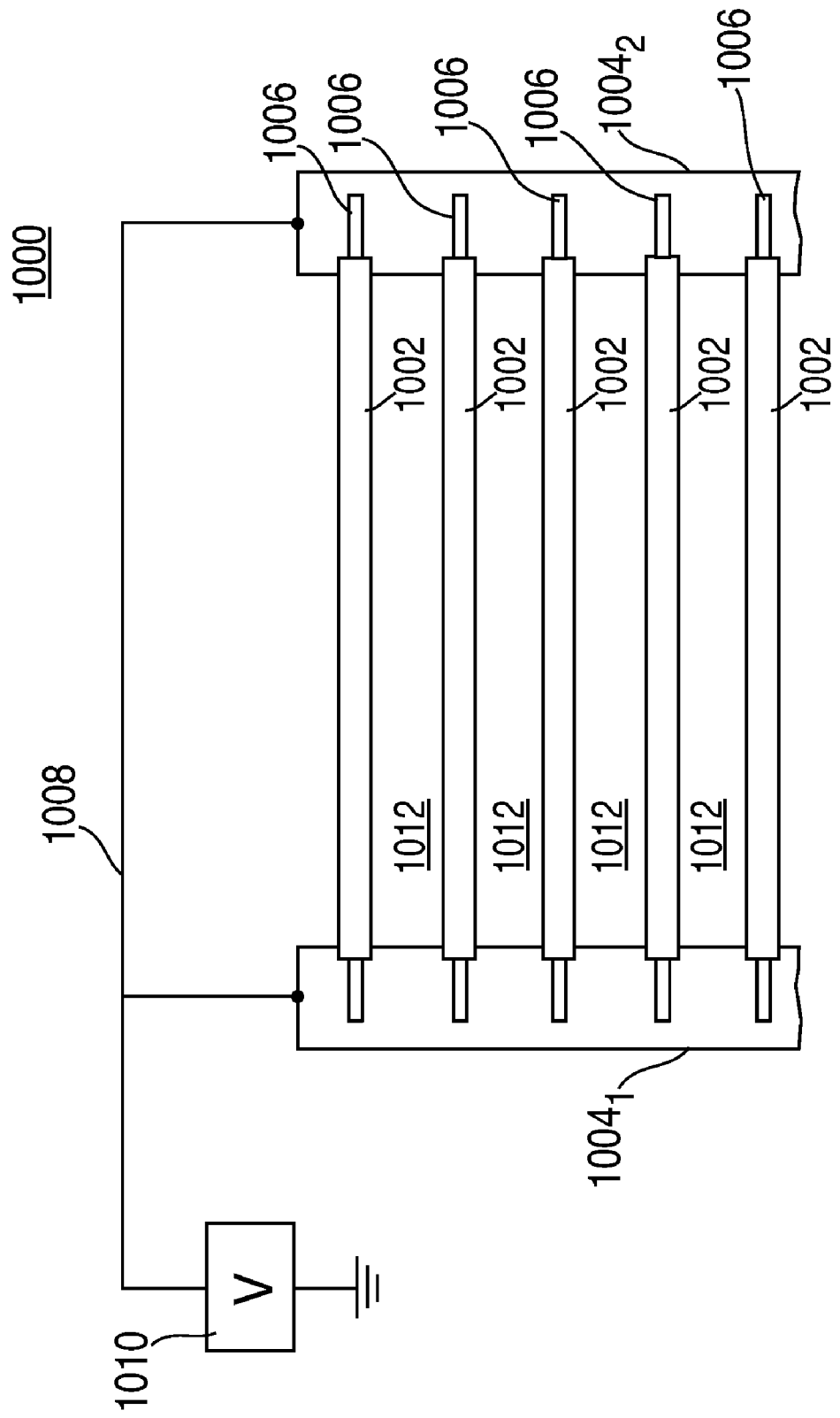
FIG. 10 is a partial top plan view of a plurality of elongated dielectric barrier members including inner electrodes connected to a voltage source through a pair of buss bars, in accordance with an embodiment of the present invention.

Referring to FIG. 10, another embodiment of non-thermal atmospheric pressure plasma cleaning device 1000, configured in a microtiter format, is provided. The device 1000 includes a plurality of elongated dielectric barrier members 1002, each containing an inner electrode (not shown), is coupled by wire 1008 to a voltage source 1010 through a pair of buss bars $1004_1$ and $1004_2$. The inner electrodes are electrically coupled to the buss bars $1004_1$ and $1004_2$ by a conductive element 1006, such as, for example, conductive wires, conductive tabs, conductive tape, conductive epoxy, and the like.

Buss bars $1004_1$ and $1004_2$ may be made of any conductive material, such as metal and metal alloys, for example, a copper and brass alloy. The elongated dielectric barrier members 1002 are made of any non-conductive material, such as, for example, ceramic, glass, plastic, polymer epoxy, or a composite of one or more such materials, such as fiberglass or a ceramic filled resin.

A plurality of probes (not shown) are introduced between the elongated dielectric barrier members 1002 that are spaced a distance from each other, as shown by 1012. The probes may be conductive and made of a conductive material, such as, for example, metal or metal alloys, or the probes may be non-conductive and made of a non-conductive material, such as, for example, plastic, glass, or any other type of material that does not conduct a current and as such would not cause a discharge to occur. In operation, power is applied to the voltage source 1010, generating a dielectric barrier discharge in the spaces 1012 between the elongated dielectric barrier members 1002 and the probes to form plasma, thereby cleaning at least a portion of each probe.

Figure 11:
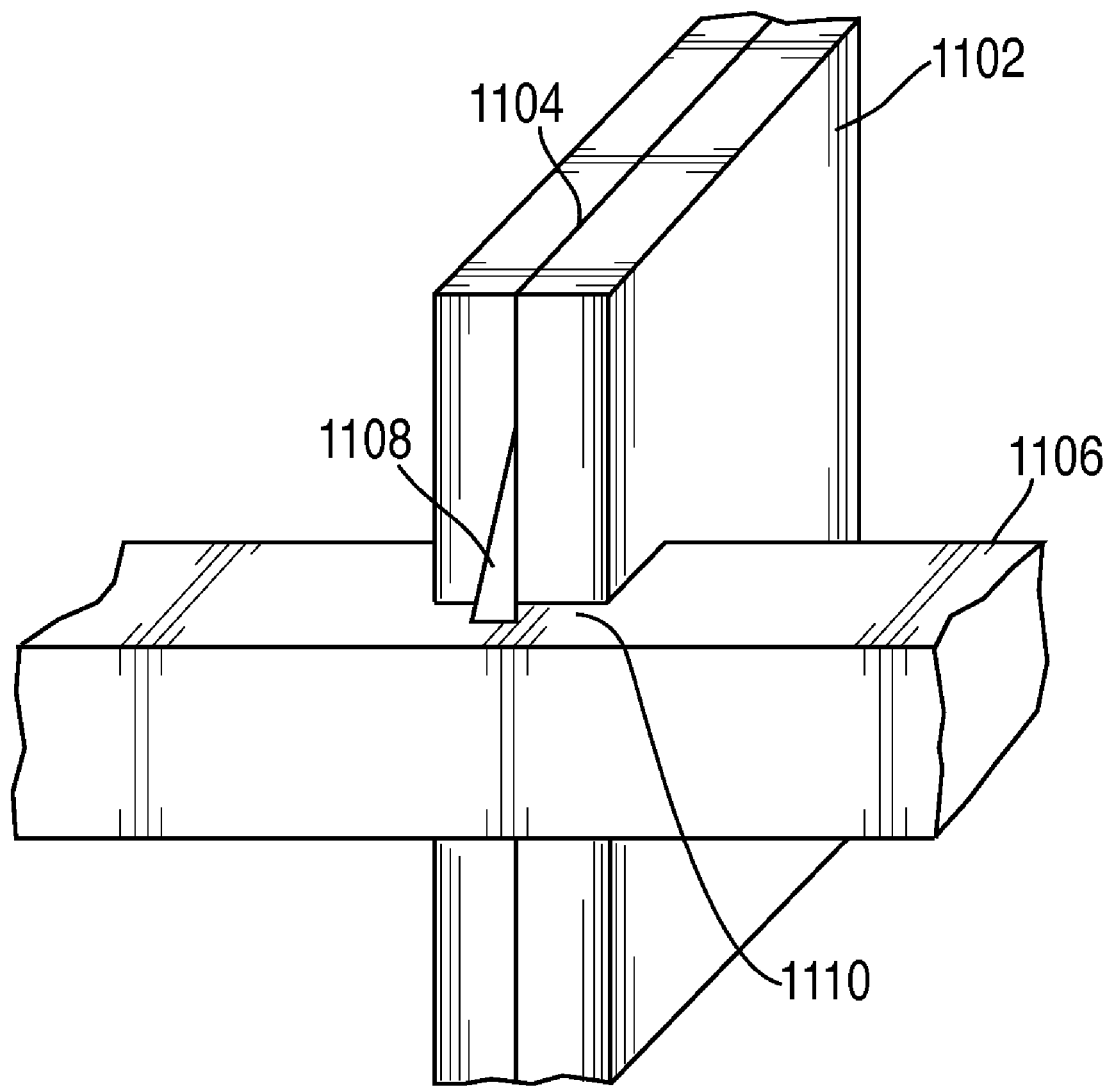
FIG. 11 is a partial side perspective view of a planar dielectric barrier plate including an inner electrode coupled to a buss bar, in accordance with an embodiment of the present invention.

Referring to FIG. 11, a partial side perspective view of an embodiment of a non-thermal atmospheric pressure plasma cleaning device is provided. A buss bar 1106 is coupled to a dielectric barrier plate 1102 as shown. The dielectric barrier plate 1002 comprises two sub-plates coupled to each other with an inner electrode 1104 provided therebetween. The buss bar 1106 may comprise a recess 1110 to securely couple the dielectric barrier plate 1102.

The electrode 1104 is electrically coupled to the buss bar 1106 by a conductive tab 1108. The conductive tab 1108 may be soldered to the electrode 1104 and the buss bar 1106 using a conductive epoxy or other conductive adhering means. The conductive tab 1108 also may be integral with the electrode 1104 and extend beyond the dielectric barrier plate 1102 sufficiently to attach to the buss bar 1106. Alternately, the electrode 1104 may be electrically coupled to the buss bar 1106 by a conductive wire, conductive tape, conductive epoxy, and the like. In operation, power is applied to the electrode 1104 through the buss bar 1106 and accordingly through the conductive tab 1108. A plasma discharge is created around the dielectric barrier plate 1102, thereby cleaning objects, such as probes, that may be introduced proximate to the dielectric barrier plate 1102.

Figure 12:
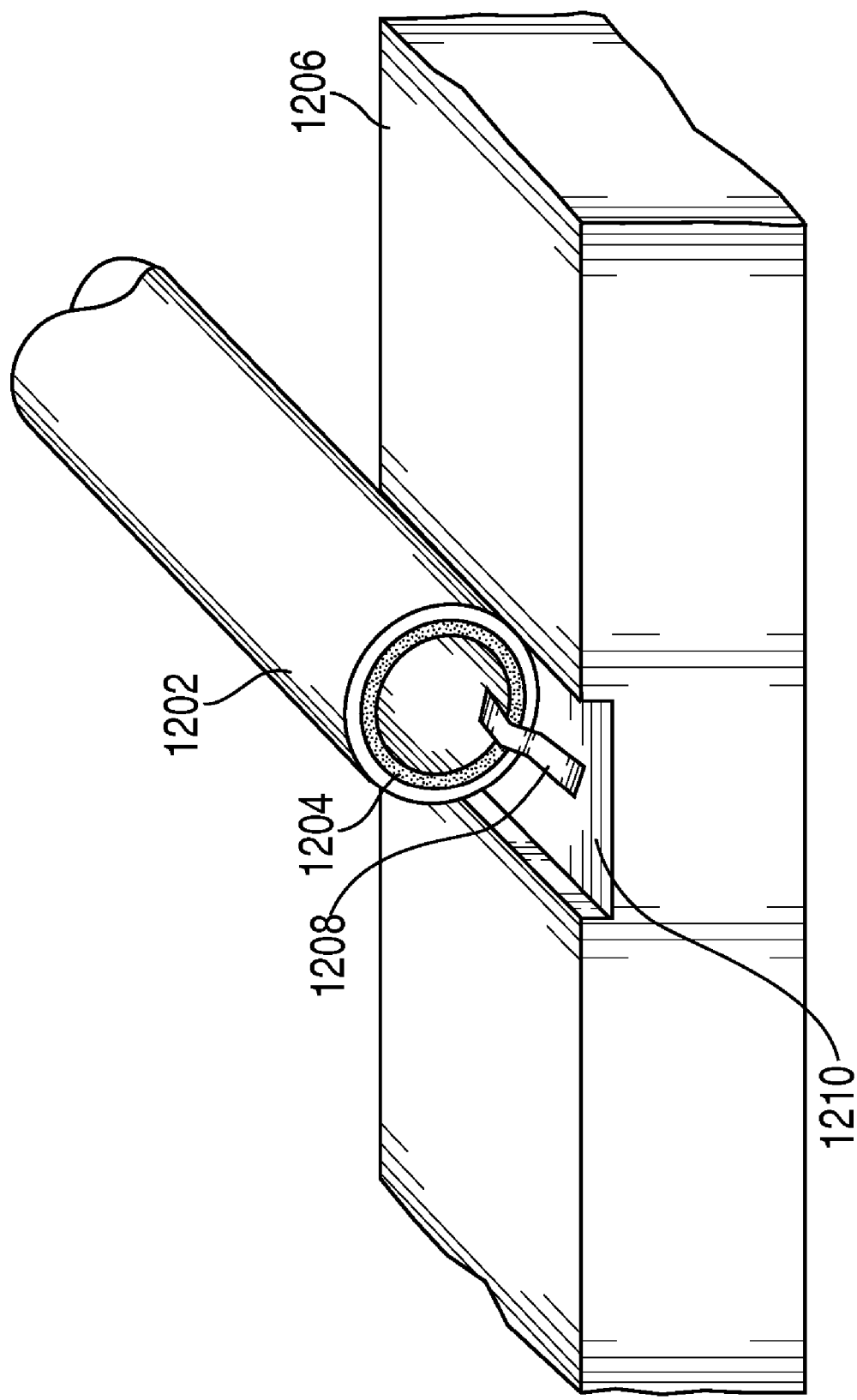
FIG. 12 is a partial side perspective view of an elongated dielectric barrier member including an inner electrode coupled to a buss bar, in accordance with an embodiment of the present invention.

FIG. 12 provides a partial side perspective view of an embodiment of a non-thermal atmospheric pressure plasma cleaning device. Similar to the embodiment described with respect to FIG. 11, a buss bar 1206 is coupled to an elongated dielectric barrier tube 1202 that contains an inner electrode 1204. The inner electrode 1204 is electrically coupled to the buss bar 1206 by a conductive wire 1208, which may be soldered onto the buss bar 1206 with a conductive epoxy. Alternately, the electrode 1204 may be electrically coupled to the buss bar 1206 by a conductive tab, conductive tape, conductive epoxy, and the like. Similar to the embodiment described with respect to FIG. 11, the buss bar 1206 may contain a recessed portion 1210 to securely couple the elongated dielectric barrier tube 1202 to the buss bar 1206.

In operation, the embodiment in FIG. 12 functions substantially similar to the embodiment described in FIG. 11, such that when power is applied to the electrode 1204 through the buss bar 1206 and accordingly through the conductive wire 1208, a plasma discharge is created around the dielectric barrier tube 1202, thereby cleaning objects, such as probes, that may be introduced proximate to the dielectric barrier tube 1202.

Figure 13A:
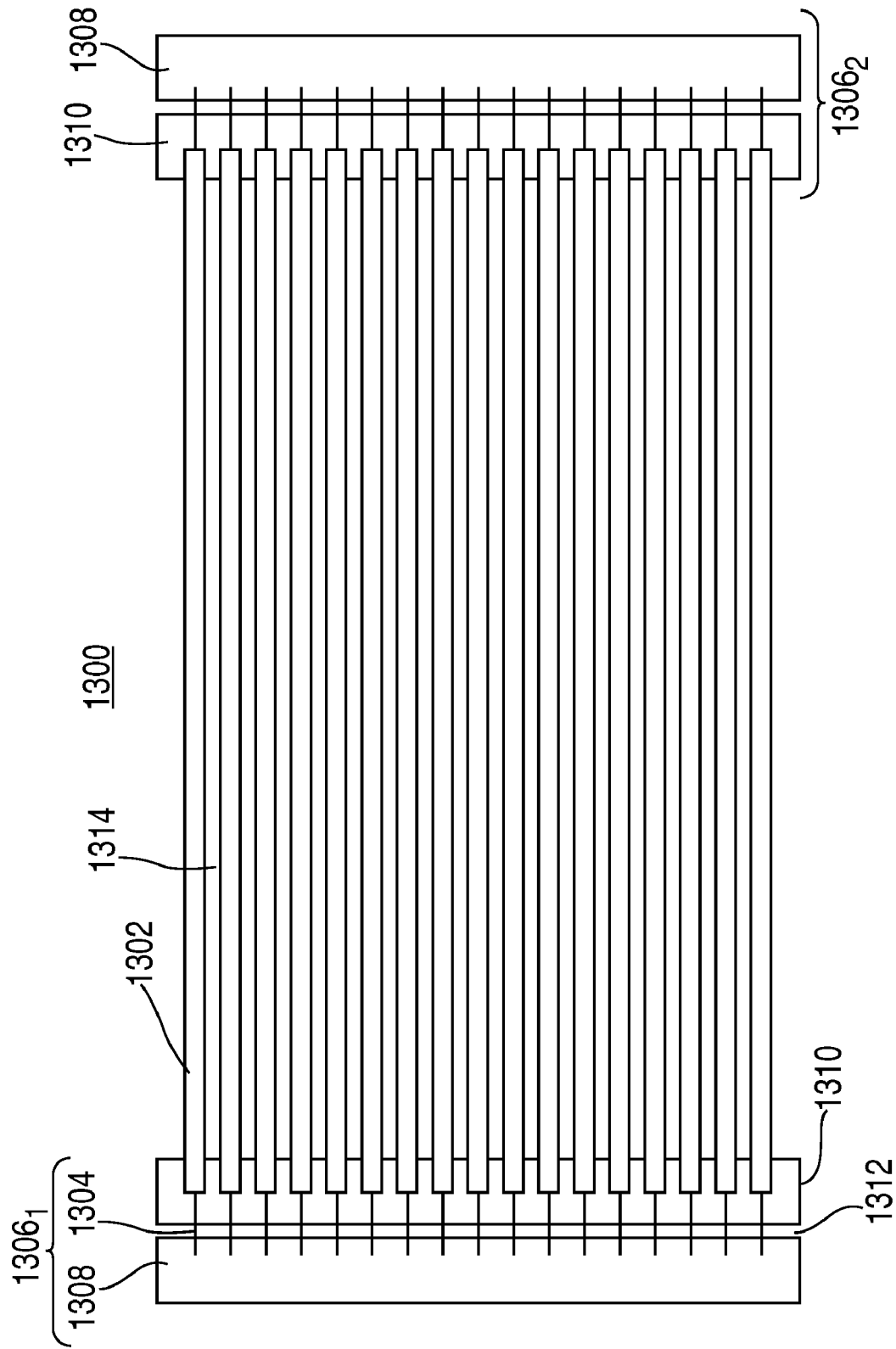
FIG. 13A is a top plan view of a plurality of elongated dielectric barrier members coupled to a pair of buss bars having flexible support members, in accordance with an embodiment of the present invention.

Referring to FIG. 13A, an embodiment of a non-thermal atmospheric pressure plasma cleaning device is provided. The device 1300 includes a plurality of elongated dielectric barrier members 1302, each containing an inner electrode (not shown) connected to a pair of buss bars 1306$_1$ and 1306$_2$. Each of the inner electrodes is coupled to a voltage source (not shown) through the buss bars 1306$_1$ and 1306$_2$ using by a conductive wire 1304. Examples of the elongated dielectric barrier members 1302 include dielectric plates, such as those described in FIG. 11, and dielectric barrier tubes, such as those described in FIG. 12.

The elongated dielectric barrier members 1302 are spaced a distance apart 1314 whereby a plurality of probes may be introduced within spaces 1314 proximate the elongated dielectric barrier members 1302 for cleaning using plasma. The buss bars 1306$_1$ and 1306$_2$ may be connected to a voltage source (not shown) where, during operation of the cleaning device, power is applied and a dielectric barrier discharge is generated in the spaces 1314 to form plasma, thereby cleaning at least a portion of each probe.

Figure 13B:
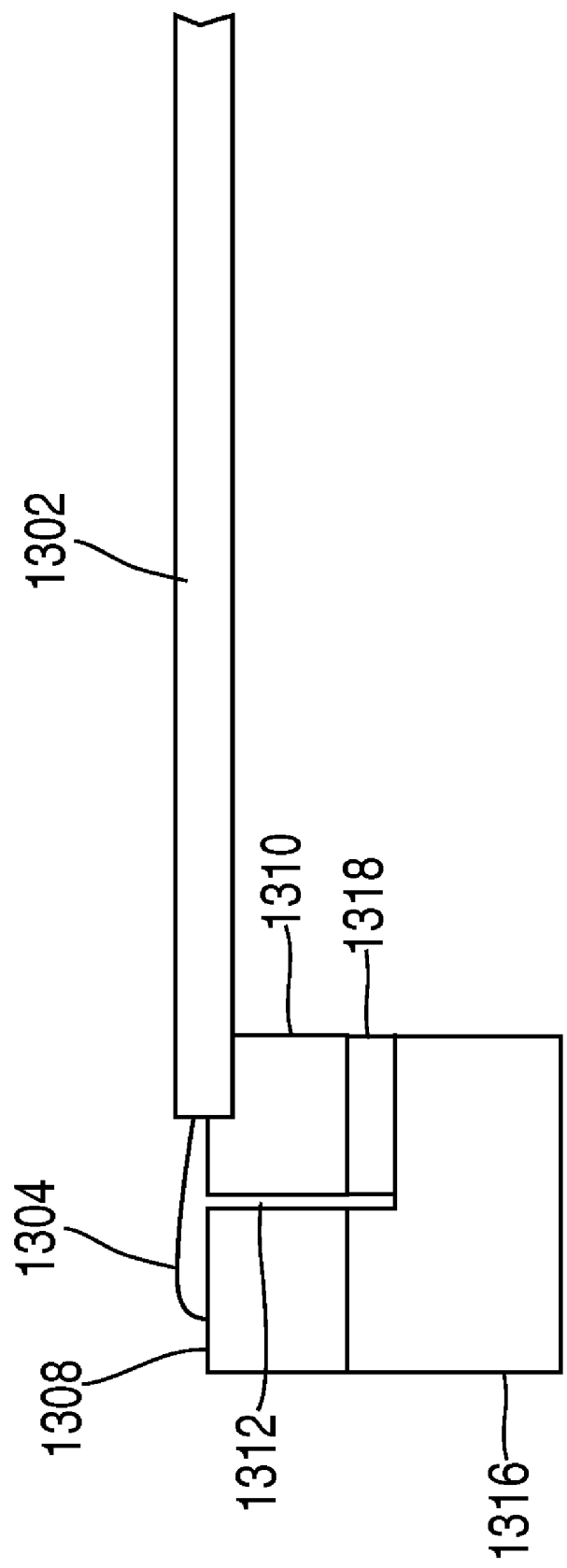
FIG. 13B is a side view of one of the dielectric barrier members, including an inner electrode, of FIG. 13A.

The buss bars 1306$_1$ and 1306$_2$ may comprise a conductive member 1308 and a flexible support member 1310 connected to a base support 1316, shown in FIG. 13B. As shown in both FIGS. 13A and 13B, the plurality of elongated dielectric barrier members 1302 rest on, are supported by, and may be attached to, the flexible support members 1310, and the inner electrodes are coupled to the conductive members 1308 by the conductive wires 1304. The conductive member 1308 may be made of any conductive material, such as metal or metal alloys, for example, a copper and brass alloy, which facilitates power flow from the voltage source to the inner electrodes through the conductive wires 1304.

The flexible support member 1310 is substantially isolated from the conductive element 1310 by a gap 1312 and functions to substantially decouple movement of each elongated dielectric barrier member 1302, with each inner electrode, from the buss bars 1306$_1$ and 1306$_2$ (FIG. 13A) during operation of the device 1300. In operation, when power is applied to the buss bars 1306$_1$ and 1306$_2$ to generate plasma, the device 1300 may generate shock vibrations, causing the elongated dielectric barrier members 1302 to vibrate with respect to the buss bars 1306$_1$ and 1306$_2$. If the elongated dielectric barrier members 1302 are directly coupled to the conductive element 1308 of the buss bars 1306$_1$ and 1306$_2$ and do not have freedom to move during the vibration, the conductive wires 1304 may break or shatter.

As shown in FIG. 13B, this problem is solved by directly coupling each of the elongated dielectric barrier members 1302 to the movable, flexible support member 1310 to allow movement of the elongated dielectric barrier members 1302 apart from the conductive member 1308 in response to shock vibration generated during operation or any other movement. Such movement substantially eliminates the risk of the conductive wires 1304 breaking or shattering. The flexible support member 1310 may be made of a fluoropolymer resin, such as polytetrafluoroethylene.

Further, as shown in 13B, the buss bars 1306$_1$ and 1306$_2$ may include an elastic support member 1318, such as, for example, an elastic gasket, between the flexible support member 1310 and the fixed support 1316, to function as a shock absorber during operation of the device 1300. The elastic member 1318 may be made of any elastomeric material conducive to high voltage systems, such as silicone and the like, for example, Silicone 30-40 Shore A.

Figure 14:
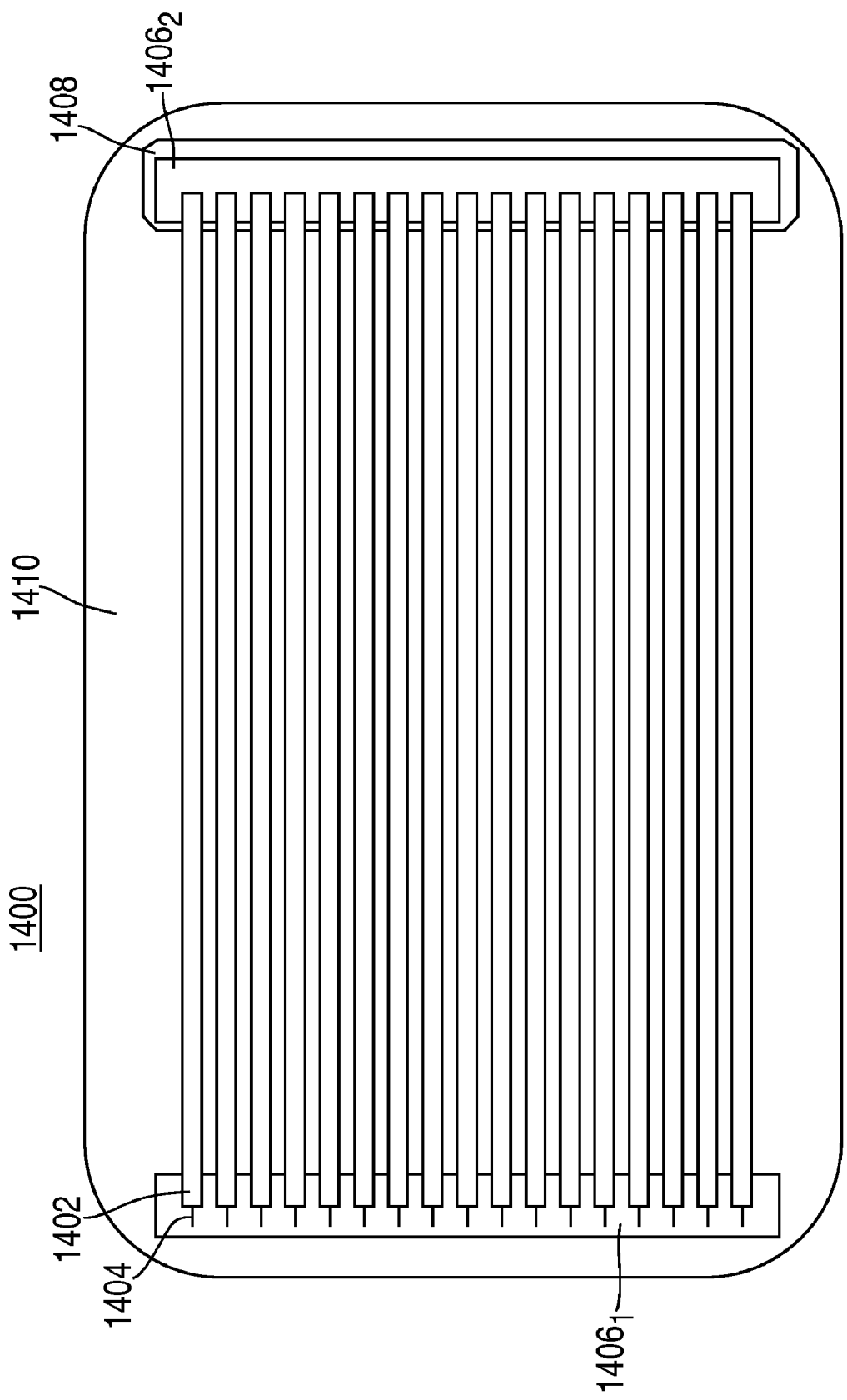
FIG. 14 is a top plan view of a plurality of elongated dielectric barrier members, including inner electrodes, coupled to a pair of buss bars, configured in a microtiter plate format, in accordance with an embodiment of the present invention.

An embodiment of a non-thermal atmospheric pressure plasma cleaning device, configured and arranged in a microtiter format 1400, is provided in FIG. 14. The microtiter format 1400 includes a plurality of elongated dielectric barrier members 1402, each containing an inner electrode (not shown) connected to a pair of buss bars 1406$_1$ and 1406$_2$. Each of the inner electrodes is coupled to a voltage source (not shown) through the buss bars 1406$_1$ and 1406$_2$. Examples of the elongated dielectric barrier members 1402 include dielectric plates, such as those described in FIG. 11, and dielectric barrier tubes, such as those described in FIG. 12. The microtiter format 1400 includes a cassette or tray enclosure 1410 encasing the components of the format 1400.

The inner electrodes may be electrically coupled to the buss bars 1406$_1$ and 1406$_2$ by conductive wires 1404 or similar means, or a conductive epoxy coating 1408, such as, for example, epoxy potting, which is applied to substantially cover the buss bar 1406$_2$. In operation, power is applied to the connected voltage source, generating a dielectric barrier discharge in the spaces between the elongated dielectric barrier members 1402 and the probes to form plasma, thereby cleaning at least a portion of each probe. The epoxy coating 1408 substantially minimizes the arcing of the dielectric barrier discharge generated during operation of the microtiter format 1400.

The plurality of elongated dielectric barrier members 1402 are spaced a distance apart to receive a plurality of probes introduced proximate elongated dielectric barrier members 1402. The microtiter format 1400 is sized to receive 96 probes proximate the elongated dielectric barrier members 1402 in accordance with a common microtiter well design as discussed herein. In other embodiments, the microtiter format 1400 is sized to receive 384 or 1536 probes proximate the elongated dielectric barrier members 1402. One of ordinary skill would reasonably recognize that the microtiter format 1400 may be designed to receive any specific number of conductive probes arranged into a microtiter well design and that the invention is not limited to the embodiment described herein.

While the foregoing is directed to embodiments of the present invention, other and further embodiments of the present invention may be devised without departing from the basic scope thereof, which is determined by the claims that follow.

What is claimed is:

1. An apparatus for cleaning objects a plurality of grounded conductive probes using plasma, comprising:
   a microplate provided with
   a plurality of elongated dielectric barrier members arranged adjacent each other;
   a plurality of electrodes, each electrode contained within and extending substantially along the length of the plurality of elongated dielectric barrier members; wherein said plurality of electrodes are spaced and positioned for receipt of the plurality of grounded conductive probes to be cleaned between adjacent electrodes; and
   at least one buss bar for electrically coupling the plurality of electrodes to a voltage source.

2. The apparatus of claim 1, further comprising conductive tabs, each coupled between respective ones of the plurality of electrodes and the at least one buss bar.

3. The apparatus of claim 1, further comprising conductive pieces of wire, each coupled between respective ones of the plurality of electrodes and the at least one buss bar.

4. The apparatus of claim 1, further comprising a conductive epoxy coating for electrically coupling each of the plurality of electrodes to the at least one buss bar.

5. The apparatus of claim 1, further comprising an epoxy coating applied to the at least one buss bar, wherein the epoxy coating prevents arcing of a dielectric barrier discharge.

6. The apparatus of claim 1, wherein the at least one buss bar comprises a conductive member and a flexible support member connected to a base support;
   wherein the flexible support member is positioned proximate the conductive member and proximate the plurality of dielectric barrier members;
   wherein the flexible support member substantially decouples movement of the plurality of dielectric barrier members and respective electrodes from the conductive member of the at least one buss bar.

7. The apparatus of claim 6, further comprising a gap between the flexible support member and the conductive member.

8. The apparatus of claim 6, wherein the flexible support member substantially comprises a fluoropolymeric material.

9. The apparatus of claim 6, wherein the flexible support member further comprises an elastomeric component to connect the flexible support member to the base support, wherein the elastomeric component absorbs shock generated during cleaning.

10. The apparatus of claim 6, wherein the at least one flexible support comprises a fluoropolymer resin.

11. The apparatus of claim 10, wherein the fluoropolymer resin comprises polytetrafluoroethylene.

12. The apparatus of claim 1, wherein the said plurality of electrodes are spaced and positioned for receipt of said plurality of grounded conductive probes which are arranged in a microtiter plate matrix format.

13. The apparatus of claim 1, wherein the at least one buss bar comprises recessed portions for receiving and supporting at least a portion of each of the plurality of elongated dielectric barrier members.

14. An apparatus for cleaning objects using plasma, comprising:
    a microplate provided with
    a plurality of elongated dielectric barrier members arranged adjacent each other;
    a plurality of electrodes each contained within, and extending substantially along the length of the plurality of elongated dielectric barrier members;
    wherein said plurality of electrodes are spaced and positions for receipt of one or more object to be cleaned between adjacent electrodes; and
    at least one buss bar for electrically coupling the plurality of electrodes to a voltage source, wherein the object to be cleaned is coupled to ground relative to said voltage source;
    wherein the at least one buss bar comprises a conductive member and a flexible support member proximate the conductive member and proximate the plurality of dielectric barrier members, wherein the flexible support member substantially decouples movement of the plurality of dielectric barrier members and respective electrodes from the conductive member of the at least one buss bar.

15. The apparatus of claim 14, further comprising conductive tabs, each coupled between respective ones of the plurality of electrodes and the conductive member.

16. The apparatus of claim 14, further comprising conductive pieces of wire, each coupled between respective ones of the plurality of electrodes and the conductive member.

17. The apparatus of claim 14, wherein the apparatus is arranged in a microtiter plate matrix format.

18. The apparatus of claim 14, wherein the at least one flexible support member is arranged to support and isolate at least a portion of each of the plurality of elongated dielectric barrier members.

* * * * *